United States Patent
Channabasavaradhya et al.

(10) Patent No.: US 8,097,412 B2
(45) Date of Patent: Jan. 17, 2012

(54) DNA-BASED TEST FOR DETECTION OF ANNUAL AND INTERMEDIATE RYEGRASS

(75) Inventors: Chandra-Shekara Aralaguppe Channabasavaradhya, Zionsville, IN (US); Michael Duane Thompson, River Falls, WI (US)

(73) Assignee: BioDiagnostics, Inc., River Falls, WI (US)

( * ) Notice: Subject to any disclaimer, the term of this patent is extended or adjusted under 35 U.S.C. 154(b) by 309 days.

(21) Appl. No.: 12/386,058

(22) Filed: Apr. 13, 2009

(65) Prior Publication Data

US 2010/0047786 A1 Feb. 25, 2010

Related U.S. Application Data

(60) Provisional application No. 61/134,871, filed on Jul. 12, 2008.

(51) Int. Cl.
*C12Q 1/68* (2006.01)
*C12P 19/34* (2006.01)
*C07H 21/04* (2006.01)

(52) U.S. Cl. ...... 435/6.1; 435/6.11; 435/6.12; 536/24.3; 536/24.33

(58) Field of Classification Search ............... None
See application file for complete search history.

(56) References Cited

U.S. PATENT DOCUMENTS

| | | |
|---|---|---|
| 4,581,333 A | 4/1986 | Kourilsky et al. |
| 4,683,195 A | 7/1987 | Mullis et al. |
| 4,683,202 A | 7/1987 | Mullis et al. |
| 4,786,600 A | 11/1988 | Kramer et al. |
| 4,800,159 A | 1/1989 | Mullis et al. |
| 4,965,188 A | 10/1990 | Mullis et al. |
| 4,996,143 A | 2/1991 | Heller et al. |
| 5,035,996 A | 7/1991 | Hartley |
| 5,283,174 A | 2/1994 | Arnold, Jr. et al. |
| 5,374,522 A | 12/1994 | Murphy et al. |
| 5,422,252 A | 6/1995 | Walker et al. |
| 5,547,842 A | 8/1996 | Hogan et al. |
| 5,565,322 A | 10/1996 | Heller |
| 5,585,481 A | 12/1996 | Arnold, Jr. et al. |
| 5,639,604 A | 6/1997 | Arnold, Jr. et al. |
| 5,641,632 A | 6/1997 | Kohne |
| 5,656,207 A | 8/1997 | Woodhead et al. |
| 5,658,737 A | 8/1997 | Nelson et al. |
| 5,683,896 A | 11/1997 | Hartley et al. |
| 5,731,148 A | 3/1998 | Becker et al. |
| 5,801,155 A | 9/1998 | Kutyavin et al. |
| 5,846,701 A | 12/1998 | Kacian et al. |
| 5,945,313 A | 8/1999 | Hartley et al. |
| 6,162,603 A | 12/2000 | Heller |
| 6,316,610 B2 | 11/2001 | Lee et al. |
| 6,346,386 B1 | 2/2002 | Elenitoba-Johnson |
| 6,727,356 B1 | 4/2004 | Reed et al. |
| 7,018,816 B2 | 3/2006 | Yates et al. |
| 7,250,497 B2 | 7/2007 | Scholl et al. |
| 7,361,746 B2 | 4/2008 | Brentano et al. |
| 7,365,176 B2 | 4/2008 | Smith et al. |
| 7,399,592 B2 | 7/2008 | Gocke et al. |
| 2007/0150978 A1 * | 6/2007 | Byrum ........................ 800/278 |

FOREIGN PATENT DOCUMENTS

| | | |
|---|---|---|
| WO | WO 90/14439 | 11/1990 |
| WO | WO 93/13121 | 7/1993 |
| WO | WO 95/32305 | 11/1995 |
| WO | WO 97/46707 | 12/1997 |
| WO | WO 97/46712 | 12/1997 |
| WO | WO 97/46714 | 12/1997 |
| WO | WO 99/39203 | 5/1999 |
| WO | WO 2005001061 A2 * | 1/2005 |

OTHER PUBLICATIONS

Abravaya, et al., Molecular Beacons as Diagnostic Tools: Technology and Applications, Clin. Chem. Lab. Med. 2003, 41(4):468-474.
Andersen, J.R. and Lübberstedt, T. (2003). Functional markers in plants. *Trends Plant Sci.* 8: 554-560.
Andersen, J.R., Jensen, L.B., Asp, T. and Lübberstedt, T. (2006). Vernalization response in perennial ryegrass (*Lolium perenne* L.) involves orthologues of diploid wheat (*Triticum monococcum*) *VRN1* and rice (*Oryza sativa*) *Hd1*. *Plant Mol Biol.* 60: 481-494.
Armstead, I.P., Turner, L.B., Farell, M., Skøt, L., Gomez, P., Montoya, T., Donnison, I.S., King, I.P. and Humphreys, M.O. (2004). Synteny between a major heading-date QTL in perennial ryegrass (*Lolium perenne* L.) and the *Hd3* heading-date locus in rice. *Theor Appl Genet.* 108: 822-828.
Charmet, G. and Balfourier, F. (1994). Isozyme variation and species relationships in the genus *Lolium* L. (ryegrasses, Graminaceae). *Theor Appl Genet.* 87: 641-649.
Floyd, D.J. and Barker, R.E. (2002). Change of ryegrass seedling root fluorescence expression during three generations o seed increase. *Crop Sci.* 42: 905-911.
Gibson, et al., A homogeneous method for genotyping with fluorescence polarization, Clinical Chemistry 43(8): 1336-1341 (1997).
Hall, M. H. (1992). Ryegrass. *Penn State Univ. Agron Facts*, 19: 1-4.
Heid, et al., Real Time Quantitative PCR, Genome Research, 6:986-994 (1996).
Heide, O.M. (1994). Control of flowering and reproduction in temperate grasses. *New Phytol.* 128: 347-362.
Holland, et al., Detection of specific polymerase chain reaction product by utilizing the 5'→3' exonuclease activity of *Thermus aquaticus* DNA polymerase, Proc. Natl. Acad. Sci. USA, 88: 7276-7280 (Aug. 1991).
Jensen, L.B., Andersen, J.R., Frei, U., Xing, Y., Taylor, C., Holm, P.B and Lübberstedt, T. (2005). QTL mapping of vernalization response in perennial ryegrass (*Lolium perenne* L.) reveals co-location with an orthologue of wheat *VRN1*. *Theor Appl Genet.* 110: 527-536.
Jung, G.A., van Wijk, A.F.P., Hunt, W.F. and Watson, C.E. (1996). Ryegrasses. In: Moser, L.E., Buxton, D.R and Casler, M.D. (eds.) Cool-season forage grasses. *Agron Monogr.* 34. ASA, Madison, Wis., pp. 605-641.

(Continued)

*Primary Examiner* — Young J Kim

(57) ABSTRACT

We have developed a novel TaqMan quantitative PCR (Q-PCR) based DNA test for detecting annual and/or intermediate ryegrass types in perennial ryegrass. This DNA test was designed using an insertion/deletion (InDel) site in the LpVRN2_2 gene. The new DNA test is more reliable, accurate, and cost effective in detecting annual and intermediate type contamination in perennial ryegrass, having a sensitivity of 0.04% in a sample size of 5000 seeds. Use of a higher sample size (12.5-fold higher compared to the SRF test) provides additional accuracy in detecting the level of contamination A forward and reverse set of primers also identified an approximately 450 bp fragment in or near the LpVRN1 promoter, the fragment being present for all perennial, but not annual, varieties tested.

9 Claims, 3 Drawing Sheets

OTHER PUBLICATIONS

Karimoto, R.S., Axelrod, B., Wolinsky, J. and Schall, E.D. (1962). The structure of annuloline, a naturally occurring oxazole alkaloid. *Tetrahedron Lett.* 3:83-85.

Konieczny, et al., A procedure for mapping *Arabidopsis* mutations using codominant ecotype-specific PCR-based markers, The Plant Journal (1993) 4(2): 403-410.

Martin, J., Storgaard, M., Andersen, C.H. and Nielsen, K.K. (2004). Photoperiodic regulation of flowering in perennial ryegrass involving a *CONSTANCE*-like homolog. *Plant Mol Biol.* 56: 159-169.

Mummenhoff, K., et al. (2001). Chloroplast DNA phylogeny and biogeography of *Lepidium* (Brassicaceae). American Journal of Botany 88 (11):2051-2063.

Ng, C.T. et al. (2005). Multiplex Real-Time PCR Assay Using Scorpion Probes and DNA Capture for Genotype-Specific Detection of *Giardia lamblia* on Fecal Samples. *J. Clinical Microbiology*, Mar. 2005, pp. 1256-1260.

Nyquist, W.E. (1963). Fluorescent perennial ryegrass. *Crop Sci.* 3: 223-226.

Payne, R.C., Scott, J.A. and Koszykowski, T.J. (1980). An esterase isenzyme difference in seed extracts of annual and perennial ryegrass. *J Seed Tech.* 5: 15-22.

Simon, et al., Use of Fluorescence Resonance Energy Transfer Hybridization Probes to Evaluate Quantitative Real-Time PCR for Diagnosis of Ocular Toxoplasmosis, J. Clinical Microbiology, 42(8):3681-3685 (Aug. 2004).

Studer, B. et al. (2006). Development of novel microsatellite marker for the grassland species *Lolium multillorum, Lolium perenne* and *Festuca pratensis*. Molecular Ecology Notes 6:1108-1110.

Szuhai, K. et al. (2001). Simultaneous A8344G heteroplasmy and mitochondrial DNA copy number quantification in Myoclonus Epilepsy and Ragged-Red Fibers (MERRF) syndrome by a multiplex Molecular Beacon based real-time fluorescence PCR. *Nucleic Acids Research*, vol. 29, No. 3 e13.

Vogel, et al., New PCR Assay for Rapid and Quantitative Detection of Human Cytomegalovirus in Cerebrospinal Fluid, J. Clinical Microbiology 34(2): 482-483 (Feb. 1996).

Warnke, et al., Genetic linkage mapping of an annual × perennial ryegrass population, Theor. App. Genet. (2004) 109:294-304.

Warnke, S.E., Barker, R.E., Brilman, L., Young, W. and Cook, R. (2002). Inheritance of supeoxide dismutase (*Sod1*) in a perennial × annual ryegrass cross and its allelic distribution among cultivars. *Theor Appl Genet.* 105: 1146-1150.

Wege, et al., SYBR Green real-time telomeric repeat amplification protocol for the repid quantification of telomerase activity, Nucleic Acids Research (2003) 31, No. 2 e3.

Whitcombe, D., J. Theaker, S. P. Guy, T. Brown, and S. Little. 1999. Detection of PCR products using self-probing amplicons and fluorescence. Nat. Biotechnol. 17:804-807.

Yang, E.C. et al. (2004). Evidence for two independent lineages of *Griffithsia* (Ceraminaceae, Rhodophyta) based on plastic protein-coding *psaA, psbA, and rbcL* gene sequences. Molecular Phylogenetics and Evolution 31: 680-688.

Latif, et al. (2001) Fluorescence Polarization in Homogeneous Nucleic Acid Analysis II: 5'-Nuclease Assay, Genome Research 11: 436-440.

\* cited by examiner

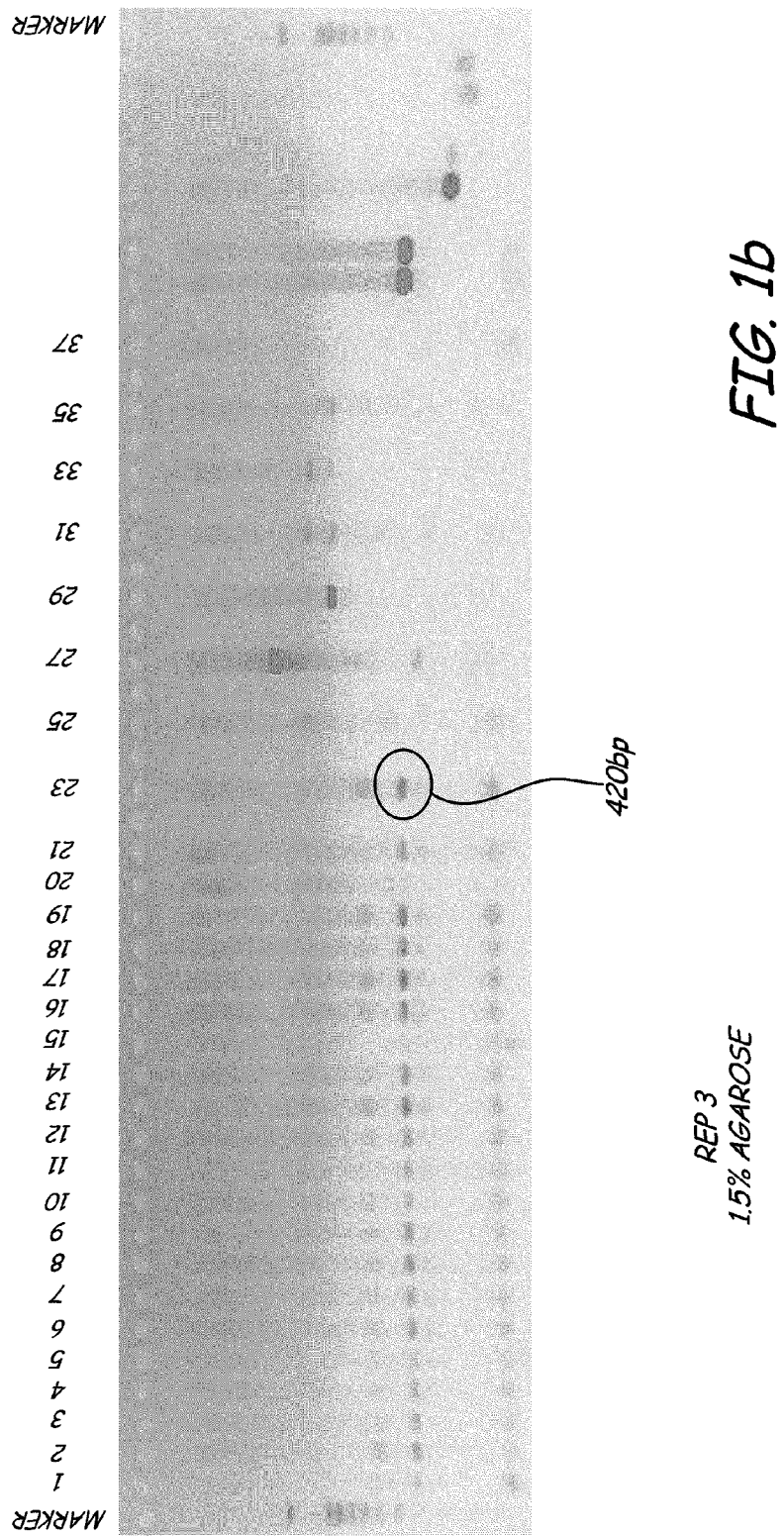

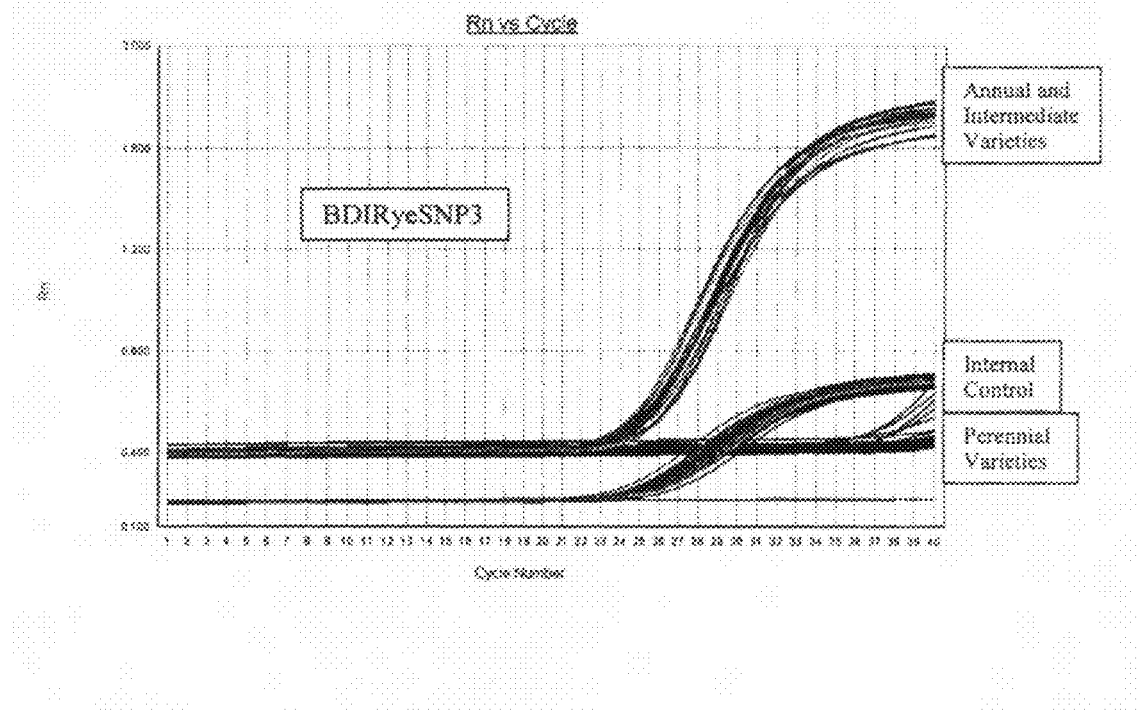
Figure 2: Amplification of annual and intermediate varieties by BDIRyeSNP3 marker with annual specific probe. Both BDIRyeSNP3 and BDIRyeIC were duplexed in a single reaction.

DNA-BASED TEST FOR DETECTION OF ANNUAL AND INTERMEDIATE RYEGRASS

CROSS-REFERENCES TO RELATED APPLICATIONS

This application claims priority under 35 U.S.C. §119 (e) to, and hereby incorporates by reference, U.S. Provisional Application No. 61/134,871, filed Jul. 12, 2008.

BACKGROUND OF THE INVENTION

1. Field of the Invention

This invention relates to detecting contaminants in seed lots. More specifically, this invention relates to detecting annual or intermediate ryegrass seed or plants in lots of perennial ryegrass seed or plants.

2. Background

Ryegrass is the most commonly used cool season grass for uses such as lawns and golf courses in the temperate regions of the world. Introduced from Europe, perennial ryegrass (*Lolium perenne* L.) is commonly used for these purposes. Perennial ryegrass, because it overwinters, does not require seeding each year. Accordingly, perennial ryegrass is the most preferred type for a permanent lawn. In contrast to perennial ryegrass, annual ryegrass (*L. multiflorum* Lam.) is used mostly as a forage crop or as a temporary ground cover. However, annual ryegrass is often present as an undesirable contaminant in perennial ryegrass seed lots. As a consequence of close proximity and due to sexual compatibility, intercrosses of annual and perennial ryegrass occur with some regular frequency, giving rise to intermediate ryegrass (*L.×hybridum* Hausskn.).

The morphologies of annual and perennial ryegrass seeds are substantially identical. Consequently, visual inspection of samples from seed lots cannot detect the presence or proportion of annual seeds in perennial ryegrass seed lots. Previous attempts to determine the contamination percentage of annual ryegrass seed in seed lots of perennial ryegrass have involved using annuloline as a marker, followed by visual observation of plants in growouts.

Annuloline is an oxazole alkaloid secreted in roots of rye grass plants bearing an allele for expression. Previously, it was believed that the annuloline-secreting allele was present only in annual ryegrass. However, the allele for annuloline secretion has been introgressed into perennial and is often present in intermediate ryegrass varieties. Accordingly, the presence of the allele conferring expression of annuloline is not a reliable indicator of whether a specific ryegrass plant is annual or perennial. Nonetheless, the International Seed Testing Association currently recommends using an annuloline-based test, termed seedling root fluorescence (SRF) and/or a growout test to estimate annual rye grass contamination in perennial ryegrass seed lots. The SRF test has thus been proven unreliable because some perennial ryegrass genotypes express the SRF trait to some degree under certain environmental or test conditions, thereby causing inaccuracies of test results. The SRF test is also laborious and time-consuming, usually requiring two to three weeks to complete. Growout tests, although reliable, are expensive to conduct and may require nearly two months to complete.

There is thus a clear and present need for an alternate, accurate test to distinguish annual and intermediate ryegrass from perennial ryegrass and to estimate the level of annual and intermediate ryegrass seed contamination in perennial ryegrass seed lots.

SUMMARY

Accordingly, there is provided a probe having an isolated nucleic acid, such isolated nucleic acid including the nucleotide sequence of SEQ ID NO: 10 or SEQ ID NO: 11 and which preferentially distinguishes annual or perennial ryegrass DNA, respectfully. Either of the foregoing probes may comprise 12 sequential nucleotides from either of SEQ ID NO: 10 or SEQ ID NO: 11 or from either of SEQ ID NO: 8 or SEQ ID NO: 9. Either probe may include a reporter bound to the nucleic acid. The reporter may utilize fluorescence resonance energy transfer in order for the annual or perennial ryegrass DND to be detected. The reporter may include a fluorophore and a quencher.

There is further provided a kit for identifying annual or intermediate ryegrass DNA, the kit including a probe having a nucleotide sequence shown in SEQ ID NO: 10, a forward primer having a nucleotide sequence shown in SEQ ID NO: 13, and a reverse primer having a nucleotide sequence shown in SEQ ID NO: 14.

There is still further provided a method for identifying annual or intermediate DNA, the method including amplifying DNA of a sample from a perennial ryegrass seed lot or plurality of tissue samples, sensing a fluorescent signal generated during said amplification, and using such fluorescent signal to estimate a proportion of annual or intermediate ryegrass DNA. The foregoing method may use a probe having a nucleotide sequence shown in SEQ ID NO: 10 or SEQ ID NO: 11 and forward and reverse primers flanking one of the foregoing probes. The forward primer may include the nucleotide sequence shown in SEQ ID NO: 10; and the reverse primer may include the nucleotide sequence shown in SEQ ID NO: 14.

There is yet further provided

All publications, patents, and patent applications cited herein are hereby incorporated by reference in their entirety.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

BRIEF DESCRIPTION OF THE FIGURES

FIGS. 1*a* and 1*b* show the results of electrophoresis of PCR products obtained from the LpVRN1 locus of perennial, intermediate, and annual ryegrass varieties.

FIG. 2 shows amplification of annual and intermediate varieties by BDIRyeSNP3 marker with annual specific probe, both BDIRyeSNP3 and BDIRyeIC being duplexed in a single reaction.

Figure 1A:
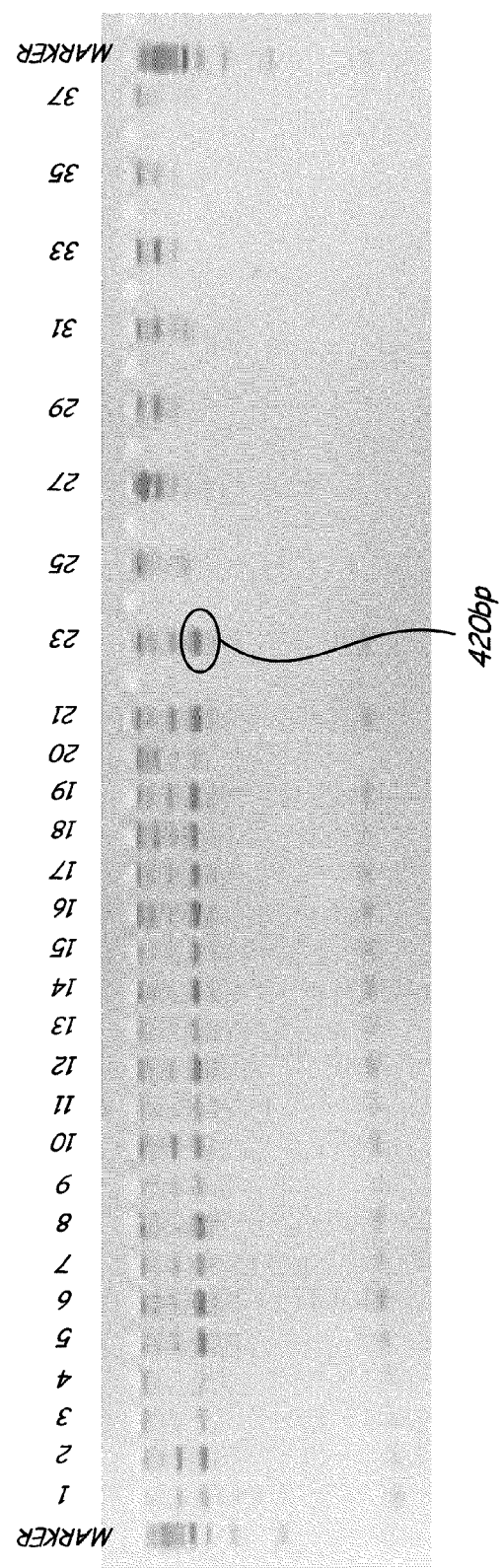

It is understood that the above-described figures are only illustrative of the present invention and are not contemplated to limit the scope thereof.

DETAILED DESCRIPTION

1. Definitions

"Amplification" is any known in vitro procedure for obtaining one or more copies of a target nucleic acid sequence, its complement, or fragments thereof, that relies on a polymerase-mediated extension of an amplification oligonucleotide or primer. In vitro nucleic acid amplification refers to production of amplified sequences that may contain less than the complete target region sequence or its complement. Such amplification methods include, for example and without limitation, transcription-mediated amplification (TMA), replicase-mediated amplification, polymerase chain reaction (PCR) amplification, and strand-displacement amplification (SDA). Replicase-mediated amplification uses self-replicating RNA molecules, and a replicase such as QB-replicase specific for the self-replicating RNA (U.S. Pat. No. 4,786,600; PCT No. WO 90/14439). PCR amplification uses a DNA polymerase such as Taq Polymerase, primers, and a series of thermal cycling reactions to synthesize multiple copies of the two complementary strands of DNA or cDNA (U.S. Pat. Nos. 4,683,195, 4,683,202, and 4,800,159; Methods in Enzymology, 1987, Vol. 155: 335-350). SDA uses a primer that contains a recognition site for a restriction endonuclease such that the restriction endonuclease nicks one strand of a hemi-modified DNA duplex that includes the target sequence, followed by amplification by a series of primer extension and strand displacement steps (Walker et al., 1992, Proc. Nat. Acad. Sci. USA 89:392-396; and U.S. Pat. No. 5,422,252). As used herein, "amplifying" may refer to the process of synthesizing nucleic acid molecules that are complementary to one or both strands of a template nucleic acid molecule (for example, target nucleic acid molecules).

"Hybridization Conditions." The invention may include nucleic acids that hybridize under stringent hybridization conditions (as defined herein) to all or a portion of the nucleotide sequence represented by any nucleotide sequence disclosed herein or its complement. The hybridizing portion of the hybridizing nucleic acids is typically at least 12 (for example, 15, 20, 25, 30, or 50) nucleotides in length. The hybridizing portion of the hybridizing nucleic acid is at least 80%, at least 95%, or at least 98% identical to the sequence of a portion, or all, of a nucleic acid encoding a nucleotide sequence disclosed herein or its complement. Hybridizing nucleic acids of the type described herein can be used, for example, as a probe or a primer (for example, a PCR primer). Hybridization of the oligonucleotide probe to a nucleic acid sample may be performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (for example, standard saline citrate (SSC) or saline sodium phosphate/EDTA (SSPE)). Then, assuming that 1% mismatching results in a 1 degree C. decrease in the Tm, the temperature of the final wash in the hybridization reaction is reduced accordingly. For example, if sequences having >95% identity with the probe are sought, the final wash temperature is decreased by 5 degrees C. In practice, the change in Tm can be between 0.5 degrees C. and 1.5 degrees C. per 1% mismatch. Stringent conditions may include hybridizing at 68 degrees C. in 5×SSC/5×Denhardt's solution/1.0% SDS, and washing in 0.2×SSC/0.1% SDS at room temperature. Moderately stringent conditions may include washing in 3×SSC at 42 degrees C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, John Wiley and Sons, N.Y. at Unit 2.10.

"Isolated," when used in reference to nucleic acids (which include gene sequences or fragments) of this invention, means that a nucleic acid molecule is present in a form other than found in nature in its original environment with respect to its association with other molecules. For example, since a naturally existing chromosome includes a long nucleic acid sequence, an "isolated nucleic acid" as used herein means a nucleic acid molecule having only a portion of the nucleic acid sequence in the chromosome, but not one or more other portions present on the same chromosome. Thus, for example, an isolated gene typically includes no more than 25 kb of a naturally occurring nucleic acid sequence which immediately flanks the gene in the naturally existing chromosome or genomic DNA. However, it is noted that an "isolated nucleic acid" as used herein is distinct from a clone in a conventional library, such as genomic DNA library and cDNA library in that the clones in a library are still an admixture with almost all the other nucleic acids in a chromosome or a cell. An isolated nucleic acid can be present in a vector.

An "Isolated nucleic acid" is a nucleic acid not identical to that of any naturally occurring nucleic acid or to that of any fragment of a naturally occurring genomic nucleic acid spanning more than three separate genes. The term therefore covers, without limitation, (a) a DNA which has the sequence of part of a naturally occurring genomic DNA molecule, but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; or (d) a recombinant nucleotide sequence that is part of a hybrid gene, for example, a gene encoding a fusion protein. Specifically excluded from this definition are nucleic acids present in mixtures of (i) DNA molecules, (ii) transfected cells, and (iii) cell clones, for example, as these occur in a DNA library such as a cDNA or genomic DNA library.

"Label" or "reporter" is a molecular moiety or compound that can be detected or lead to a detectable response, label and reporter being synonymous in meaning. A label may be joined, directly or indirectly, to a nucleic acid probe or to the nucleic acid to be detected, for example, to an amplified nucleic acid. Direct labeling can occur through bonds or interactions linking the label to the probe, for example, covalent bonds or non-covalent interactions. Indirect labeling can occur through use of a bridging moiety or "linker", for example, an additional oligonucleotide, which is directly or indirectly labeled. Labels may include any known detectable moiety, for example, radionuclide, ligand such as biotin or avidin, enzyme or enzyme substrate, reactive group, chromophore such as a dye or colored particle, luminescent compound such as a bioluminescent, phosphorescent or chemiluminescent compound, or fluorescent compound. For example, the label on a labeled probe is detectable in a homogeneous assay system, i.e., in a mixture, bound labeled probe exhibits a detectable signal compared to unbound labeled probe; see U.S. Pat. Nos. 5,283,174 and 5,639,604. Suitable labels for use in a homogenous assay are chemiluminescent compounds, such as acridinium ester ("AE") compounds (U.S. Pat. Nos. 5,656,207, 5,658,737 and 5,639,604). Methods of attaching labels to nucleic acids and detecting labels are known in the art, for example, see Sambrook et al., Molecular Cloning, A Laboratory Manual, 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174 and 4,581,333; and EP Pat. App. No. 0 747 706.

"Nucleic acid" is a multimeric compound comprising nucleosides or nucleoside analogs having nitrogenous heterocyclic bases, or base analogs, in which the nucleosides are covalently linked via a backbone structure to form a polynucleotide. Nucleic acid includes conventional ribonucleic acid (RNA) and deoxyribonucleic acid (DNA), and analogs thereof. A nucleic acid backbone may comprise a variety of known linkages, including, for example, one or more of sugar-phosphodiester linkages, peptide-nucleic acid bonds (PCT No. WO 95/32305), phosphorothioate linkages, methylphosphonate linkages or combinations thereof. Sugar moieties of the nucleic acid may be ribose or deoxyribose, or similar compounds containing substitutions, for example, 2' methoxy substitutions and/or 2' halide substitutions. Nitrogenous bases may be conventional bases, such as adenine (A), guanine (G), cytosine (C), thymine (T) uracil (U), known analogs thereof (for example, inosine (I) and others, such as described in The Biochemistry of the Nucleic Acids 5-36, Adams et al., ed., 11th ed. (1992), or known derivatives of purine or pyrimidine bases (PCT No. WO 93/13121) and "abasic" residues in which the backbone includes no nitrogenous base for one or more residues (U.S. Pat. No. 5,585, 481). A nucleic acid may comprise only conventional sugars, bases and linkages, as found in RNA and DNA, or may include both conventional components and substitutions (for example, conventional bases linked via a methoxy backbone, or a nucleic acid containing a mixture of conventional bases and one or more base analogs). For all of the sequences presented herein as DNA sequences, it is understood that the disclosed sequence also discloses the RNA equivalent (substituting a U for T residues), the reverse sequence and the reverse complement of the disclosed sequence. It is additionally understood that each disclosed sequence also includes any translated protein or polypeptide, including any equivalent sequences disclosing such protein or polypeptide.

An "oligonucleotide" or "oligomer" is a nucleic acid having generally less than about 1,000 residues, including polymers in a size range having a lower limit of about two to five nucleotide residues and an upper limit of about 500 to 900 nucleotide residues. Suitable oligomers are in a size range having a lower limit of about five to about 15 residues and an upper limit of about 50 to 600 residues; or in a range having a lower limit of about 10 residues and an upper limit of about 100 residues. Oligomers may be purified from naturally occurring sources, but may be synthesized using known methods.

"Percent Homology" of two amino acid sequences or of two nucleic acids may be determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (for example, XBLAST and NBLAST) are used. See http://www.ncbi.nlm.nih.gov.

"Primer," is used to refer to a relatively short nucleic acid fragment or sequence, which can be DNA, RNA, a hybrid thereof, a chemically modified analog, or a derivative thereof. Typically, a primer is single-stranded. However, a primer can also be double-stranded having two complementing strands that can be separated by denaturation. A primer may have a length of from about eight nucleotides to about 200 nucleotides, from about 12 nucleotides to about 100 nucleotides, or from about 15 to about 50 nucleotides. A primer can be labeled with a detectable marker or modified in any conventional manner for various molecular biological applications.

"Probe" is a nucleic acid oligomer that hybridizes specifically to a target sequence in a nucleic acid or its complement, such as in an amplified nucleic acid, under conditions that promote hybridization, thereby allowing detection of the nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A "target" of a probe generally refers to a sequence within, i.e., a subset of, an amplified nucleic acid sequence, that hybridizes specifically to at least a portion of a probe oligomer using hydrogen bonding, i.e., base pairing. "Sufficiently complementary" sequences allow stable hybridization of a probe oligomer to a target sequence in selected hybridization conditions, even if the two sequences are not 100% complementary. A probe may be labeled or unlabeled, depending upon the detection method used.

"Promoter" refers to a polynucleotide molecule that is involved in recognition and binding of RNA polymerase II and other proteins (trans-acting transcription factors) to initiate transcription. A plant promoter may be a native or non-native promoter that is functional in plant cells. A promoter can be used as a 5' regulatory element for modulating expression of an operably linked transcribable polynucleotide molecule. Promoters may be defined by their temporal, spatial, or developmental expression pattern.

"Sample" is any tissue or material, such as derived from *Lolium* species. For example, one or more seeds, plants, or parts of plants such as leaf, stem, root, pollen or ovule. To prepare the sample for analysis, the biological sample may be treated to physically disrupt cell structure and release intracellular nucleic acids into a solution that may contain other components (for example, enzymes, buffers, salts, detergents and the like). Such methods are known in the art, for example in U.S. Pat. Nos. 5,374,522, 5,641,632, and 5,846,701.

"Thermostable polymerase" is a polymerase enzyme that is heat stable, i.e., the enzyme catalyzes the formation of primer extension products complementary to a template and does not irreversibly denature when subjected to elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermusfervidus*. Nonetheless, polymerases that are not thermostable also can be employed in PCR assays if the enzyme is replenished after each cycle thereof.

Unless defined otherwise, all scientific and technical terms used herein have the same meaning as commonly understood by those skilled in the relevant art. General definitions of many such terms are found in, for example Glossary of Crop Science Terms, Crop Science Society of America, Madison, Wis. (1992), Dictionary of Microbiology and Molecular Biology, 2nd ed. (Singleton et al., 1994, John Wiley & Sons, New York, N.Y.), or The Harper Collins Dictionary of Biology (Hale & Marham, 1991, Harper Perennial, New York, N.Y.). Unless otherwise described, the techniques employed or contemplated herein are standard methodologies well known to those of ordinary skill in the art.

2. Polymerase Chain Reaction (PCR)

U.S. Pat. Nos. 4,683,202, 4,683,195, 4,800,159, and 4,965,188 disclose conventional polymerase chain reaction (PCR) techniques. PCR typically employs two oligonucleotide primers that bind to a selected nucleic acid template (for example, DNA or RNA). Primers useful in the present invention include oligonucleotide primers capable of acting as a point of initiation of nucleic acid synthesis proximate a target sequence. A primer can be purified from a restriction digest by conventional methods or the primer can be produced synthetically. The primer may be single-stranded for maximum efficiency in amplification, but the primer may also be double-stranded. Double-stranded primers are first denatured, i.e., treated to separate the strands. One method of denaturing double stranded nucleic acids is by heating.

If the template nucleic acid is double-stranded, it is necessary to separate the two strands before the template nucleic acid can be used as a template in PCR. Strand separation can be accomplished by any suitable denaturing method including physical, chemical, or enzymatic. One method of separating the nucleic acid strands is heating the nucleic acid until it is predominately denatured, for example, greater than 50%, 60%, 70%, 80%, 90% or 95% denatured. Heating conditions necessary for denaturing template nucleic acid will depend, for example, on the buffer salt concentration and the length and nucleotide composition of the nucleic acids being denatured, but typically range from about 90 degrees C. to about 105 degrees C. for a time length depending on features of the reaction such as temperature and the nucleic acid length. Denaturation is typically conducted from about 30 seconds to four minutes.

If the double-stranded nucleic acid is denatured by heat, the reaction mixture is allowed to cool to a temperature that promotes annealing of each primer to its target sequence on the nucleic acid to be amplified. The temperature for annealing is usually from about 35 degrees C. to about 65 degrees C. Annealing times can be from about 10 seconds to about one minute. The reaction mixture is then adjusted to a temperature at which the activity of the polymerase is promoted or optimized, i.e., a temperature sufficient for extension to occur from the annealed primer such that products complementary to the template nucleic acid are generated. The temperature should be sufficient to synthesize an extension product from each primer that is annealed to a nucleic acid template, but should not be so high as to denature an extension product from its complementary template. By way of illustration and not limitation, the temperature for extension generally ranges from about 40 degrees to 80 degrees C. Extension times can be from about 10 seconds to about five minutes.

PCR assays can employ target nucleic acid such as DNA or RNA, including messenger RNA (mRNA). The template nucleic acid may or may not be purified. If not purified, the template DNA may be a minor fraction of a complex mixture, such as genomic nucleic acid extracted from seeds or plant vegetative or reproductive tissues. DNA or RNA may be extracted from a biological sample such as seeds or plants by routine techniques such as those described in Diagnostic Molecular Microbiology: Principles and Applications (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with other PCR reagents under reaction conditions that induce primer extension, for example, 50 mM KCl, 10 mM Tris-HCl (pH 8.3), 1.5 mM $MgCl_2$, 0.001% (w/v) gelatin, 0.5-1.0 µg denatured template DNA, 50 pmoles of each oligonucleotide primer, 2.5 U of Taq polymerase, and 10% dimethylsulfoxide (DMSO). PCR reactions usually contain between about 150 and 320 µM each of dATP, dCTP, dTTP, dGTP, or one or more analogs thereof.

The newly synthesized strands form a double-stranded molecule that can be used in succeeding steps of the reaction. The steps of strand separation, annealing, and elongation can be repeated as often as needed to produce the desired quantity of amplification products corresponding to the target nucleic acid molecule. The limiting factors in the reaction are the amounts of primers, thermostable enzyme, and nucleoside triphosphates present in the reaction. The cycling steps of denaturation, annealing, and extension are usually repeated at least once. For use in detection, the number of cycling steps will depend, for example, on the nature of the sample. If the sample is a complex mixture of nucleic acids, more cycling steps are usually required to amplify the target sequence sufficiently for detection. Generally, the cycling steps are repeated at least about 20 times, but may be repeated as many as 40, 60, or 100 times.

3. Electrophoresis & Southern Blotting

When used in detection of target sequences, PCR assays per se require the use of conventional methods such as gel electrophoresis and Southern blotting for detection of amplified target DNA. These methods may be labor intensive and may frequently require more than one day to complete. Additionally, the manipulation of amplification products for the purpose of detection (for example, by blotting) increases the risk of carry-over contamination and false positives. Further disadvantages of current PCR methods for detecting a target DNA sequence may include poor standardization of reagents and product amplification conditions and the lack of general availability for use in all diagnostic laboratories. However, in situations where the presence or absence, but not necessarily the proportion, of a target sequence, such as annual or intermediate ryegrass DNA, is desired, this invention includes using electrophoresis and Southern blotting.

4. Fluorescence Resonance Energy Transfer (FRET)

Fluorescence Resonance Energy Transfer ("FRET") technology, disclosed in, for example, U.S. Pat. Nos. 4,996,143, 5,565,322, 5,849,489, and 6,162,603, is based on the phenomena that, when a donor fluorescent moiety and a corresponding acceptor fluorescent moiety are positioned within a specific distance of each other, energy transfer takes place between the two fluorescent moieties. This transferred energy can be detected and/or quantified. An oligonucleotide probe containing a fluorescent moiety can hybridize to an amplification product at a particular position determined by the complementarity of the oligonucleotide probe to the target nucleic acid sequence. Upon hybridization of the oligonucleotide probe to the amplification product at the appropriate positions, a FRET signal is generated. Hybridization temperatures can range from about 35 degrees C. to about 65 degrees C. for about 10 seconds to about one minute.

Fluorescent analysis can be carried out using, for example, a photon counting epifluorescent microscope system (containing the appropriate dichromic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties, "corresponding" refers to an acceptor fluorescent moiety having an emission spectrum overlapping the excitation spectrum of the donor fluorescent moiety. The wavelength maximum of the emission spectrum of the acceptor fluorescent moiety may be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for high efficiency Forster energy transfer, a large final Stokes shift (e.g., >100 nm), shift of the emission as far as possible into the red portion of the visible spectrum (e.g., >600 nm); and shift of the emission to a higher wavelength than the Raman water fluorescent emission produced by excitation at the donor excitation wavelength. For example, a donor fluorescent moiety can be chosen with an excitation maximum near a laser line (for example, Helium-Cadmium 442 nm or Argon 488 µm), a high extinction coefficient, a high quantum yield, and a good overlap of its fluorescent emission with the excitation spectrum of the corresponding acceptor fluorescent moiety. A corresponding acceptor fluorescent moiety can be chosen with a high extinction coefficient, a high quantum yield, a good overlap of its excitation with the emission of the donor fluorescent moiety, and emission in the red part of the visible spectrum (>600 nm).

Representative donor fluorescent moieties which can be used with various acceptor fluorescent moieties in FRET technology, by way of illustration and not limitation, may include 5-carboxy fluorescein, 6-carboxy fluorescein (FAM), 6 carboxy-4',5'-dichloro-2',7'-dimethoxyfluorescein, 2',4',1,4,-tetrachlorofluorescein (TET), 2',4',5',7',1,4,-hexachlorofluorescein (HEX), 2-dimethoxy-4',5'-dichloro-6-carboxyrhodamine (JOE), 2'-chloro-7'-phenyl-1,4-dichloro-6-carboxyfluorescein (VIC), carboxy-rhodamine 6G (R6G), 3-carboxypentyl-3'-ethyl-5,5'-dimethyl oxacarbocyanine (CYA), 3-(carboxypentyl)-1'-ethyl-3,3,3',3'-tetramethyl-5,5'-disulphonato carbocyanine (CY3), 2'-chloro-5'-fluoro-7',8'-fused phenyl-1,4-dichloro-6-carboxyfluorescein (NED), Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives.

Representative acceptor or quencher fluorescent moieties, depending upon the donor fluorescent moiety used, by way of illustration and not limitation, may include 6-carboxy-tetramethylrhodamine (TAMRA or TMR), dimethylaminoazosulphonic acid (DABCYL), 4-dimethylaminophenylazobenzenesulfonyl acid (DABSYL), nitrothiazole blue (NTB), anthraquinone, malachite green, nitrothiazole, 3-(carboxypentyl)-1'-ethyl-3,3,3',3'-tetramethyl-4,5,4',5'-(1,3(disulphonato)dibenzo-carbocyanine) (CY3.5), 1-(carboxypentyl)-1'-ethyl-3,3,3',3'-tetramethyl-5,5'-disulphonato-dicarbocyanine (CY5), 1-(carboxypentyl)-1'-ethyl-3-3,3'-3'-tetramethyl-4-5-4'-5-(1,3-disulphonato)-dibenzodicarbocyanine (CY5.5), 1-(carboxypentyl)-1'-ethyl-3,3,3',3'-tetramethyl-5,5'-disulphonato-tricarbocyanine (CY7), 6-carboxyrhodamine (Rhodamine 110), 5-carboxyrhodamine-6G (R6G or REG-5), 6-carboxyrhodamine-6G (R6G-6 or REG-6), LC™-Red 640, LC™-Red 705, Cy5.5, Lissamine rhodamine B sulfonyl chloride, tetramethyl rhodamine isothiocyanate, rhodamine×isothiocyanate, erythrosine isothiocyanate, diethylenetriamine pentaacetate or other chelates of Lanthanide ions (for example, Europium, or Terbium). Donor and acceptor fluorescent moieties can be obtained, for example, from Molecular Probes (Junction City, Oreg.) or Sigma Chemical Co. (St. Louis, Mo.).

Minor groove binders may also be present in, or associated with, the primers or probes of this invention. Suitable minor groove binders by way of illustration and not limitation may include dihydrocyclopyrroloindole tripeptide (DPI3), Hoechst 33258, netropsin, distamycin, a trimer of 3-carbamoyl-1,2-dihydro-(3-H7)-pyrrolo[3,2-e]indole-7-carboxylate (CDPI$_3$), a pentamer of N-methylpyrrole-4-carbox-2-amide (MPC$_5$), and pyrrolo[4,5-e]indolin-7-yl}carbonyl)pyrrolo[4,5-e]indolin-7-yl]carbonyl}pyrrolo[4,5-e]indoline-7-carboxylate (DPI$_3$).

Also present in, or associated with, the primers and probes of this invention by way of illustration and not limitation may be a reference dye such as tetrapropano-6-carboxy-rhodamine (ROX).

A minor groove binding dye may also be associated with the primers and probes of this invention. Suitable minor groove binding dyes by way of illustration and not limitation may include SYBR® Green 1,4-[(3-methyl-6-(benzothiazol-2-yl)-2,3-dihydro-(benzo-1,3-thiazole)-2-methylidene)]-1-methyl-pyridinium iodide (BEBO), 1-methyl-4-[(3-methyl-2(3H)-benzothiazolylidene)methyl]-pyridinium iodide (BO), 4',6-diamidino-2-phenylindole (DAPI).

The donor and acceptor fluorescent moieties can be attached to a probe oligonucleotide via a linker arm. The length of each linker arm may be important, as the linker arms will affect the distance between the donor and acceptor fluorescent moieties. The length of a linker arm for the purpose of the present invention is the distance in Angstroms from the nucleotide base to the fluorescent moiety. In general, a linker arm is from about 10 to about 25 Angstroms in length. The linker arm may be of the kind described in WO 84/03285, which also discloses methods for attaching linker arms to a particular nucleotide base and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide may include thiourea linkers (FITC-derived, for example, fluorescein-CPG's from Glen Research or ChemGene, Ashland, Mass.), amide-linkers (fluorescein-NHS-ester-derived, such as fluorescein-CPG from BioGenex, San Ramon, Calif.), or 3'-amino-CPG's that require coupling of a fluorescein-NHS-ester after oligonucleotide synthesis.

5. Quantitative PCR (QPCR)

The invention provides a qualitative and quantitative assay for detecting annual or intermediate ryegrass (target) DNA.

Identical PCR cycling conditions are used for both the qualitative and quantitative assays. The quantitative levels of target DNA are determined by processing samples containing known amounts of target nucleic acid as standards along with samples with known levels of annual or intermediate ryegrass seed or vegetative tissue.

For instance, the Applied Biosystems 7500 Real Time PCR System (Applied Biosystems, Foster City, Calif.) detects and quantifies nucleic acids in standard 96-well formats by using a thermal cycling system, software to activate and control the system, and reagents to quantify the target nucleic acids. Such reagents include the TaqMan® Fast Universal PCR Master Mix, TaqMan® Universal PCR Master Mix, and Power SYBR® Green PCR Master Mix. The ABI 7500 Real Time 7500 System can detect 10 copies of template nucleic acid in a 50 µl reaction at a 99.7% level of confidence in a run time of two hours or less. The ABI 7500 Real Time 7500 System has an optical system including a CCD camera with halogen lamp excitation and five emission filters for FAM®/SYBR® Green, VIC®/JOE™, NED™/TAMRA™/Cy3, ROX™/ Texas Red®, and Cy5 for reaction volumes of between 20 and 100 µl.

By way of another nonlimiting example, the LightCycler PCR assay as disclosed in U.S. Pat. No. 7,365,176 is an automated, real-time system for the qualitative and quantitative detection of target DNA. The system is rapid (two to three hours total sample preparation and analytical time), sensitive (detects ≧ 10 copies of target DNA/sample), specific (detects target DNA exclusively), and has a wide dynamic linear range of $10^1$ to $10^7$ copies of target DNA/sample. By using commercially available real-time PCR instrumentation (for example LightCycler™, Roche Molecular Biochemicals, Indianapolis, Ind.), PCR amplification and detection of the amplification product can be combined in a single closed cuvette with dramatically reduced cycling time. Since detection occurs concurrently with amplification, the real-time PCR methods obviate the need for manipulation of the amplification product and diminish the risk of cross-contamination between amplification products. Real-time PCR thus greatly reduces turn-around time and is an attractive alternative to conventional PCR techniques in the laboratory.

The PCR method of U.S. Pat. No. 7,365,176 provides methods for detecting the presence or absence of target DNA in a biological sample from an individual seed or plant. Methods provided by the invention, to the extent possible, avoid problems of sample contamination, false negatives, and false positives. The methods include performing at least one cycling step that includes amplifying a target portion of a nucleic acid molecule from a sample using a pair of primers. Each of the primers anneals to a target within or adjacent to a target nucleic acid molecule such that at least a portion of each amplification product contains nucleic acid sequence corresponding to the target sequence. The amplification product contains the nucleic acid sequences that are complementary to the probes. The amplification product is produced, provided that target nucleic acid is present. Each cycling step further includes contacting the sample with a probe. According to the invention, such probe is labeled with a donor fluorescent moiety and a corresponding acceptor fluorescent moiety. The presence or absence of FRET between the donor fluorescent moiety and the corresponding acceptor fluorescent moiety is detected during extension and consequent degradation of the probe.

Each cycling step includes an amplification step and a hybridization step, each cycling step usually followed by a FRET detecting step. Multiple cycling steps are performed, preferably in a thermocycler. Methods of the invention can be performed using the primer and probe sets to detect the presence of the target DNA such as annual and intermediate ryegrass DNA.

If amplification of target nucleic acid occurs and an amplification product is produced, the step of hybridizing results in a detectable signal based upon FRET between the moieties present in the probe. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of target DNA in the sample, and the absence of FRET indicates the absence of target DNA in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within 45 cycling steps is indicative of presence of target DNA.

Melting curve analysis is an additional step that can be included in a cycling profile. Melting curve analysis is based on the fact that a nucleic acid sequence melts at a characteristic temperature called the melting temperature (Tm), which is defined as the temperature at which half of the DNA duplexes have separated into single strands. The melting temperature of a specific DNA (or other nucleotide) depends primarily upon its nucleotide composition. Thus, a DNA molecule rich in G and C nucleotides has a higher Tm than one with an abundance of A and T nucleotides. By detecting the temperature at which the FRET signal is lost, the melting temperature of probes can be determined. Similarly, by detecting the temperature at which signal is generated, the annealing temperature of probes can be determined. The melting temperature(s) of the probes from the amplification product can confirm the presence or absence of target in the sample.

Within each thermocycler run, control samples are cycled as well. Positive control samples can amplify target nucleic acid control template (for example, a nucleic acid other than that of the target) using, for example, control primers and control probes. Positive control samples can also amplify, for example, a construct containing a target nucleic acid molecule. Such a control can be amplified internally (for example, within the sample) or in a separate sample run side-by-side with the samples from which contamination is to be determined. Each thermocycler run may also include a negative control that, for example, lacks target template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment of this invention, the methods of the invention include steps to avoid contamination. For example, an enzymatic method utilizing uracil-DNA glycosylase is described in U.S. Pat. Nos. 5,035,996, 5,683,896, and 5,945, 313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in diagnostic laboratory handling samples.

Conventional PCR methods in conjunction with FRET technology can be used to practice the methods of the invention. In one embodiment, a LightCycler™ instrument is used. A detailed description of the LightCycler™ System and real-time and on-line monitoring of PCR can be found at biochem.roche.com/lightcycler. The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler™ thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples. The LightCycler™ carousel housing the cuvettes can be removed from the instrument. Therefore, samples can be loaded outside of the instrument (in a PCR clean room, for example). This feature also allows for the sample carousel to be easily cleaned and sterilized. The fluorometer, as part of the LightCycler™ apparatus, houses the light source. The emitted light is filtered and focused by an illumination lens onto the top of the cuvette. Fluorescent light emitted from the sample is then focused by the same lens, passed through a dichroic mirror, filtered appropriately, and focused onto data-collecting photohybrids. The optical unit available in the LightCycler™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As described herein, amplification products can also be detected using labeled hybridization probes that take advantage of FRET technology. One format of FRET technology utilizes two hybridization probes. Each probe can be labeled with a different fluorescent moiety and is generally designed to hybridize in close proximity to the other probe in a target DNA molecule (for example, an amplification product). A donor fluorescent moiety, for example, fluorescein, is excited at 470 nm by the light source of the LightCycler™ Instrument. During FRET, the fluorescein transfers its energy to an acceptor fluorescent moiety such as a LightCycler®-Red 640 (LC™-Red 640) or LightCycler™-Red 705 (LC™-Red 705). The acceptor fluorescent moiety then emits light of a longer wavelength, which is detected by the optical detection system of the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules, for example, the number of target genomes.

a. Taqman® Technology a. One FRET protocol, described for example by Heid et al., Real Time Quantitative PCR, Genome Res. 6:986-994 (1996), utilizes TaqMan® technology to detect the presence or absence of an amplification product, and hence, the presence or absence of target DNA. See also, Holland, Detection of Specific Polymerase Chain Reaction Product by Utilizing the 5' 3' Exonuclease Activity of *Thermus aquaticus*, Proc. Natl. Acad. Sci. USA, 88: 7276-7280 (August 1991). TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during subsequent elongation. As a result, the excited fluorescent moiety and the quencher moiety become spatially separated from one another. As a consequence of this spatial separation and upon excitation of the first fluorescent moiety in the absence of the quencher, the fluorescence emission from the first fluorescent moiety can be detected. By way of example, an ABI PRISM® 7500 Sequence Detection System (Applied Biosystems, Foster City, Calif.) uses TaqMan® technology, and is suitable for performing the methods described herein for detecting the presence of a target DNA sequence. Information on PCR amplification and detection using an ABI PRISM® 7500 system can be found at appliedbiosystems.com/products. In one embodiment of the Taqman® technology, one fluorescent dye, 6-carboxyfluorescein ("FAM"), servers as a reporter at the 5' end of the oligonucleotide. A second fluorescent dye, 6-carboxy-tetramethyl-rhodamine ("TAMRA"), is positioned at the 3' end. The emission spectra of FAM are quenched by TAMRA as long as the two dyes are in close proximity on the probe. Stated otherwise, when the probe is intact, fluorescent energy transfer occurs and the reporter die fluorescent omission from FAM is absorbed by the quenching die TAMRA. However, upon nuclease degradation of the probe in the extension phase of PCR, the degradation releases the quenching of the FAM fluorescent emission, thereby resulting in an increase in peak fluorescent emission at 518 nm. Upon cleavage and degradation of the probe, the reporter die emission is no longer transferred efficiently to the quenching die, resulting in an increase of the reporter die fluorescent emission spectra. Use of a sequence detector, such as an ABI Prism® 7500 Sequence Detector, allows measurement and quantification of fluorescent emissions of large numbers of samples in a single run, for example, 96 wells of a thermal cycler, continuously during PCR amplification. Accordingly, the reactions are monitored in real time. A TaqMan® probe and primers are also obtained for a gene common to all of perennial, annual, and intermediate ryegrass for use as a control. One suitable gene common to the foregoing species is β-tubulin.

b. Molecular Beacons

Molecular beacons in conjunction with FRET can also be used to detect the presence of an amplification product using real-time PCR methods of the invention. Molecular beacon technology uses a hybridization probe labeled with first and second fluorescent moieties. The second fluorescent moiety is generally a quencher and the fluorescent labels are typically located at each end of the probe. Molecular beacon technology uses a probe oligonucleotide having a sequence permitting secondary structure formation, for example, a hairpin. As a result of secondary structure within the probe, both fluorescent moieties are in spatial proximity when the probe is in solution. However, after hybridization to a target nucleic acid (i.e., amplification template or product), the secondary structure of the probe is disrupted and the fluorescent moieties become separated such that, upon excitation with light of a suitable wavelength, the emission of the first fluorescent moiety can be detected. Advantages of Molecular Beacons are that they 1) fluoresce only when bound to their targets, 2) can be labeled with a fluorophore of any desired color, and 3) are so specific that they discriminate between single-nucleotide polymorphisms. See, for example, Kramer, Introduction to Molecular Beacons at http://molecular-beacons.org/Introduction.HTML (as of 1 Aug. 2008); and Abrabaya, et al., Molecular-beacons as Diagnostic Tools: Technology and Applications, Clin. Chem. Lab. Med. 41(4):468-474 (2003).

c. Scorpions®

As disclosed in Whitcombe et al., Detection Of PCR Products Using Self-probing Amplicons and Fluorescence, Nature Biotechnology 17: 804-807 (August 1999), detection of PCR products is accomplished with self-probing amplicons. A Scorpions Primer carries a 5' extension comprising a probe element, a pair of self-complimentary stem sequences, and a fluorophore/quencher pair. The extension is "protected" from being copied by the inclusion of a blocking hexethylene glycol (HEG) monomer. After a round of PCR extension from a primer, a newly synthesized target region is now attached to the same strand as the probe. Following a second round of denaturation and annealing, the probe and target hybridize, the probe subsequently fluorescing.

d. Double Stranded DNA-Binding Dyes

As an alternative to FRET, an amplification product can be detected using a double-stranded DNA binding dye such as a fluorescent DNA binding dye (for example, SYBRGreenI® or SYBRGold® (Invitrogen Corp., Carlsbad, Calif.)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product. See U.S. Pat. No. 6,346,386.

e. Fluorescence Polarization i. Fluorescence polarization is disclosed by Gibson, et al., A Homogeneous Method for Genotyping With Fluorescence Polarization, Clinical Chemistry 43: (8) 1336-1341 (1997) and combines the amplification refractory mutation system (ARMS™) and fluorescence polarization to thereby provide a homogeneous genomic DNA genotype analysis method. Oligonucleotide probes labeled with, for example, fluorescein dyes fluorescein isothiocyanate and 5-([4,6-di-chlorotriazin-2-yl]amino)fluorescein and the rhodamine dye, 6-carboxyrhodamine, may be included in amplification mixes to anneal to PCR Products after amplification. Hybridization is accompanied by an increase in fluorescence polarization of the probe.

8. Plant Materials Used in the Examples

Genetically pure and blends of perennial and ryegrass variety seed lots were obtained from five different sources. A total of 32 pure perennial, 26 pure annual, and two intermediate of varieties were used to test specificity of the DNA markers of this invention. Additionally, 41 perennial varieties with varying levels of annual rye grass seed contamination were used to test the accuracy of the DNA tests of this invention. A standard growout protocol was followed as set forth by the Oregon State University Seed Laboratory, with the exception that all seedlings were transplanted without prior selection based on SRF. The transplanted seedlings and evaluation was conducted in a Conviron® plant growth chamber (Controlled Environments Limited, Winnipeg, Canada), wherein adequate growth conditions were maintained. The results of visual ratings for growth habit are presented below.

9. Examples

A. Example 1

DNA Extraction from Seeds

One thousand seeds from each ryegrass seed lot were manually counted and weighed. An appropriate seed weight equivalent to 5000 seeds was then estimated and used for DNA extraction. Each sample was then ground in a one-half pint jar using clean blenders. Approximately ½ ml of the finely ground seed material was sampled in a 96-well matrix plate. Four replications of ground seeds per sample were collected for DNA extraction. The DNA extraction was carried out using Qiagen Gentra Puregene Cell Kits (catalog numbers 158908 (cell lysis solution) and 158912 (protein precipitation solution); Qiagen Inc., 19300 Germantown Road, Germantown, Md. 20874) following the manufacturer's instructions and using a BioMek FX Laboratory WorkStation (Beckman Coulter, Inc., 4300 N. Harbor Boulevard, Fullerton, Calif. 92834-3100). Six hundred µl of (5 prime) cell lysis solution (Fisher Scientific Item # FP2301330) was added to a tube containing each 0.5 ml of ground seed material in each sample. The tubes were then sealed and agitated for two minutes. The tubes were subsequently centrifuged briefly at 3000 rpm. After being incubated at 65 degrees C. for 20 minutes, the tubes were again centrifuged for 30 seconds at 3000 rpm. Then, 200 µl of 5 Prime Protein Precipitation Solution (Fisher Scientific Item # FP23011350) was added to each tube, the tubes then being resealed, agitated for one minute, and centrifuged for 10 minutes at 3000 rpm. Two hundred µl of supernatant from each sample was transferred to a new tube containing 200 µl isopropanol (2-propanol), the new tubes then being resealed, gently inverted 20 times, then centrifuged for 10 minutes at 3000 rpm. The supernatant was then poured off and 200 µl of 70% ethanol was added to each tube. The tubes were then resealed, gently shaken for 30 seconds to loosen the pellets from the tube walls, then centrifuged for three minutes at 3000 rpm. The supernatant was again poured off from each tube and the sample within each tube blotted dry on a clean absorbent surface and air-dried upside down form 10 minutes. After adding 100 µl of DNase-free water to each well in a 0.8 ml plate, the DNA pellet was resuspended by repeated pipetting. As an alternative to repeated pipetting, the DNA pellet could have been resuspended by being incubated at 65 degrees C. for one hour.

B. Example 2

DNA Extraction from Plant Tissues

For individual plant DNA extractions, the plants were germinated from seeds on paper towels following a standard germination protocol, wherein seeds were planted atop blotters wetted at a rate of twice the weight of the dry blotters with a 0.02% potassium nitrate solution. After a five day pre-chill at 10 degrees C., the seed was transferred to a chamber, wherein temperatures were 10 degrees C. for 16 hours and 25 degrees C. for eight hours until germination (between 14 and 21 days). Two to three week old seedlings were individually sampled into a 96-well plate and DNA was extracted from at least four plants per variety using Qbiogene FastDNA® kits (MP Biomedicals, 2251 Rutherford Road, Carlsbad, Calif. 92008) following the manufacturer's instructions. In this protocol, lead shot, 200 μl CLS-VF lysing solution, and 50 μl protein precipitation solution (PPS) was added to each well in 1.2 ml plates. The plates were then heat-sealed and shaken for three minutes. The plates were subsequently centrifuged for five minutes at 3000 rpm. Subsequently, 150 μl binding matrix was dispensed into 0.8 ml plates and 150 μl supernatant was then added from corresponding 1.2 ml plates. The 0.8 ml plates were then sealed with easy-peel, shaken for one minute. The supernatant was then poured off and the plates placed upside down on dry absorbent under-pads to dry for five minutes. Two hundred μl salt ethanol wash (SEWS) was subsequently added, the plates sealed, agitated for 30 seconds, and centrifuged for one minute at 3000 rpm. The supernatant was poured off after centrifugation and the plates were allowed to dry after being placed upside down on absorbent under pads for 10 minutes, then placed right side up for 30 minutes. One hundred μl TE was then added to the 0.8 ml plates, the plates sealed, left for 10 minutes, agitated for 30 seconds, and centrifuged for one minute at 3000 rpm. Subsequently, 50 μl DNA was transferred to new 0.8 ml plates and the new plates were then centrifuged for 3 minutes at 3000 rpm. Dilution (⅕) was accomplished by adding 40 μl TE and 10 μl DNA to new 0.8 plates.

C. Example 3

Chloroplast Markers

Chloroplast-specific regions psbA and trnT-trnL were investigated using a cleaved amplified polymorphic sequence (CAPS) analysis. Respective annual and perennial forward and reverse primers used in PCR for locus psbA are listed in SEQ ID NO: 17, SEQ ID NO: 18, SEQ ID NO: 19, and SEQ ID NO: 20. The nucleotide sequence for the psbA locus is shown in SEQ ID NO: 21 (GenBank Accession AF363674). While no nucleotide sequences are shown herein, BDIRye-CAP5 (restriction endonuclease SpeI) was the designation used by the inventors. Contrary to published sequences, the CAPS analysis showed no SNPs between the annual and perennial ryegrass genotypes tested. Respective annual and perennial forward and reverse primers for locus trnT-trnL are shown in SEQ ID NO: 22, SEQ ID NO: 23, SEQ ID NO: 24, and SEQ ID NO: 25 for a first set termed BDIRyeCAP7, wherein Hinf I was used as the restriction endonuclease. Respective annual and perennial forward and reverse forward and reverse primers for locus trnT-trnL are shown in SEQ ID NO: 26, SEQ ID NO: 27, SEQ ID NO: 28, and SEQ ID NO: 29 for a second set termed BDIRyeCAP8, wherein Ras I was used as the restriction endonuclease. The nucleotide sequence for trnT-trnL is present in SEQ ID NO: 30 (GenBank Accession AY450935). In contrast to published sequences, the CAPS analysis showed no conserved SNPs present in either of the chloroplast regions (data not shown).

D. Example 4

LM28

An SSR marker, LM28, identified by Struder et al., Development of Novel Microsatellite Markers for the Grassland Species, *Lolium multiflorum, Lolium perenne* and *Festuca pratensis*, Molecular Ecology Notes 6: 1108-1110 (2006) is represented by SEQ ID NO: 1 and forward and reverse primers for LM28 are shown in SEQ ID NO: 2 and SEQ ID NO: 3, respectively. The sequences for perennial and annual ryegrass varieties were determined for this region. LM 28 was found to distinguish perennial from annual and intermediate ryegrass DNA. However, the SSR assay requires individual plant testing and is a gel-based procedure. Accordingly, the required SSR assay is comparatively expensive and cannot be used for a high through-put procedure as may be required by some embodiments of this invention.

E. Example 5

LPVRN1

To the inventors' knowledge, there were no reports comparing vernalization genes LpVRN1, LpVRN2_2, or LpVRN2_3 (LpCO) or between annual and perennial ryegrass varieties. Accordingly, DNA sequences of LpVRN1 and LpVRN2_2 gene regions in 10 perennial and five annual varieties were compared. The primer sequence of Andersen et al. (2006) was used for DNA sequencing. It is important to note that, while the objective of the study carried out by Andersen et al. identified genes involved in vernalization, it did not address genes involved in annual vs. perennial growth habit.

The PCR amplification of a portion of the LpVRN1 promoter region shown in SEQ ID NO: 4 involved 20 perennial and seven annual varieties, using the forward and reverse primers of SEQ ID NO: 5 and SEQ ID NO: 6, respectively, indicated that there is a difference in the primer binding region between the two species. As can be seen from FIGS. 1a and 1b, a clear and distinct amplification of a 420 base pair fragment was present in all perennial varieties and absent in all annual varieties. The 420 bp sequence for the *L. multiflorum* variety Veyo is shown in SEQ ID NO: 31 and a corresponding 95 bp sequence for the *L. perenne* variety Falster is shown in SEQ ID NO: 32. Both were depicted in Andersen (2006). This similarity between FIGS. 1a and 1b suggested that the LpVRN1 promoter could be used in distinguishing between annual and perennial ryegrass DNA. In FIG. 1a, the results of electrophoresis in a 3.5% agarose gel are shown and wherein the band identifying the approximately 420 base pair fragment is depicted. Pure perennial varieties are represented in lanes 1-17, 19, 21, and 23. Intermediate ryegrass varieties, crosses, and segregates of crosses between annual and perennial ryegrasses, are represented in Lanes 18 and 20. Annual ryegrass varieties are represented in Lanes 25, 27, 29, 31, 33, 35, and 37, arg1 in lane 25, arg2 in lane 27, arg3 in lane 29, arg4 in lane 31, arg5 in lane 33, arg6 in lane 35, and arg7 in lane 37. In FIG. 1b, the results of electrophoresis in a 1.5% agarose gel are shown and in which the perennial, intermediate, and annual varieties and lane distinctions are identical to those of FIG. 1a. In FIG. 1b, the 420 base pair fragment is also shown and in which the presence or absence of the 420 base pair fragment is identical to that depicted in FIG. 1a.

F. Example 6

LpVRN2_2

Sequencing the LpVRN2_2 and LpCO regions (LpCO present in SEQ ID NO: 33) resulted in 11 single nucleotide polymorphisms (SNPs) and two insertion/deletion (InDel) sites in the LpVRN2_2 region. There were no conserved polymorphisms found at the LpCO region distinguishing between annual and perennial varieties (data not shown). Two of the 11 SNPs at the LpVRN2_2 region were tested using a TaqMan®-based real-time PCR assay. However, these SNPs failed to distinguish between all of the annual and perennial varieties tested (data not shown).

Accordingly, a TaqMan® probe designed to detect one of the InDel polymorphisms in LpVRN2_2 showed differentiation between annual/intermediate and perennial ryegrass varieties. As shown in Table 1, the conserved InDel site has two cytosine insertions in all perennial ryegrass varieties tested, or conversely, two cytosine nucleotide deletions in all annual ryegrass varieties tested. Two other InDel sites and 17 SNPs are present as well.

As shown in Tables 2 and 3, comparison of the published DNA sequence polymorphism between the perennial varieties Veyo and Falster, which have contrasting vernalization requirements as reported by Andersen et al. (2006) (SEQ ID NO: 7), was found to be completely different from the polymorphism observed by the inventors between annual (SEQ ID NO: 8) and perennial (SEQ ID NO: 9) ryegrass varieties.

TABLE 1

Alignment Between Determined Sequences for Annual and Perennial Ryegrass at Locus LpVRN2_2

```
Multi   8 TATTTATAGCGGAACACGGAGCGGGTGAAAGGACGTTTTGTCAGTCGAATGAAGCTCTCA  67
          ||||  ||||||||||||||||||||||||| |||||||||||||||||||| ||||
Peren  10 TATTTGTAGCGGAACACGGAGCGGGTGAAAGGTCGTTTTGTCAGTCGAATGAAGCGCTCA  69

Multi  68 ACGCCATCAGTAATGGGGGATGACCC--TCCTTCCTCGCCCTCTGAAAGGCAGGTGTATG 125
          | |||| |||||||| | ||||||||  |||||||||||||||| ||||||| ||||||
Peren  70 ATGCCAGCAGTAATGGTGGATGACCCCCTCCTTCCTCGCCCTCTGAGAGGCAGCTGTATG 129

Multi 126 TAGCTGGGTTTTTCCATGTAGCAGATTGGCCTGTAGCATCCTACGATGCACCTAAGCATG 185
          |||||||| ||||||||||||||||| |||||||||||||| ||||||||||||||||
Peren 130 TAGCTGGGGTTTTCCATGTAGCAGATCGGCCTGTAGCATCCTGCGATGCACCTAAGCATG 189

Multi 186 ATGCCGTACATTGCTCAGCTATTTATTTTAGTCTTT--CTTCAGCACCGTGATCGTCAGT 243
          ||||||||||||||||||||||||||||| ||||||  ||||||||||||||||||||||
Peren 190 ATGCCGTACATTGCTCAGCTATTTATTTTGTCTTTGTCTTCAGCACCGTGATCGTCAGT 249

Multi 244 TTACAGCAGAGGTTTGTATTCACGGTGCTTTTCTTGTAACAAATCTCCCTTTTCTCTCT 303
          |||||||||||| | |||||||||||| ||||||||||| ||||||||| ||||||||
Peren 250 TTACAGCAGAGGGTCGTATTCACGGTGTTTTTCTTGTAACAGATCTCCCTCTTTCTCTCT 309

Multi 304 CAGAACTCGGAAATAGCCAACTTAATTGTACACTGATATGAGGTATTGAGGTGC-ATATG 362
          ||||| || ||||||||||||||||||||||||||||||||||||||||||||| |||||
Peren 310 CAGAATTCAGAAATAGCCAACTTAATTGTACACTGATATGAGGTATTGAGGTGCAATATG 369

Multi 363 TGATATGTTTGTA 375
          |||||||||||||
Peren 310 TGATATGTTTGTA 382
```

Multi, annual ryegrass
Peren, perennial ryegrass

TABLE 2

Comparison of Published LpVRN2_2 Sequence and Determined Annual Sequence

```
Publi 100 AGCGGGTGAAAGGTCGTTTTGTCAAGTCGAATGAAGCGCTCAATGCCAGCAGTAATGGTG 159
          ||||||||||||| |||||||||| |||||||||| ||||| |||| |||||||||||| |
Multi  27 AGCGGGTGAAAGGACGTTTTGTCA-GTCGAATGAAGCTCTCAACGCCATCAGTAATGGGG  85

Publi 160 GATGACCCCCTCCTTCCTCGCCCTCTGAGAGGCAGCTGTATGTAGCTGGGGTTTTCCATG 219
          ||||||||   |||||||||||||||||| |||||||| ||||||||||| ||||||||
Multi  86 GATGACCC--TCCTTCCTCGCCCTCTGAAAGGCAGGTGTATGTAGCTGGGTTTTTCCATG 143

Publi 220 TAGCAGATCGGCCTGTAGCATCCTGCGATGCACCTAAGCATGATGCCGTACATTGCTCAG 279
          ||||||||  |||||||||||||| |||||||||||||||||||||||||||||||||||
Multi 144 TAGCAGATTGGCCTGTAGCATCCTACGATGCACCTAAGCATGATGCCGTACATTGCTCAG 203

Publi 280 CTATTTATTTTTGTCTTTGTCTTCAGCACCGTGATCGTCAGTTTACAGCAGAGGGTCGTA 339
          |||||||||||  ||||||  ||||||||||||||||||||||||||||||||| |||
Multi 204 CTATTTATTTTAGTCTTT--CTTCAGCACCGTGATCGTCAGTTTACAGCAGAGGTTTGTA 261

Publi 340 TTCACGGTGTTTTTCTTGTAACAGATCTCCCTCTTTCTCTCTCAGAATTCAGAAATAGCC 399
          ||||||||| |||||||||||||| ||||||| |||||||||||||  || |||||||||
Multi 262 TTCACGGTGCTTTTCTTGTAACAAATCTCCCTTTTTCTCTCTCAGAACTCGGAAATAGCC 321

Publi 400 AACTTAATTGTACACTGATATGAGGTATTGAGGTGCATATGTGATATGTTTGT 452
          |||||||||||||||||||||||||||||||||||||||||||||||||||||
Multi 322 AACTTAATTGTACACTGATATGAGGTATTGAGGTGCATATGTGATATGTTTGT 374
```

Publi, sequence published in Andersen et al. (2006)
Multi, determined annual ryegrass sequence

TABLE 3

Comparison of Published LpVRN2_@ Sequence and Determined Perennial Sequence

```
Publi 100 AGCGGGTGAAAGGTCGTTTTGTCAAGTCGAATGAAGCGCTCAATGCCAGCAGTAATGGTG 159
          |||||||||||||||||||||||| ||||||||||||||||||||||||||||||||||
Peren  29 AGCGGGTGAAAGGTCGTTTTGTCA-GTCGAATGAAGCGCTCAATGCCAGCAGTAATGGTG  87

Publi 160 GATGACCCCCTCCTTCCTCGCCCTCTGAGAGGCAGCTGTATGTAGCTGGGGTTTTCCATG 219
          ||||||||||||||||||||||||||||||||||||||||||||||||||||||||||||
Peren  88 GATGACCCCCTCCTTCCTCGCCCTCTGAGAGGCAGCTGTATGTAGCTGGGGTTTTCCATG 147

Publi 220 TAGCAGATCGGCCTGTAGCATCCTGCGATGCACCTAAGCATGATGCCGTACATTGCTCAG 279
          ||||||||||||||||||||||||||||||||||||||||||||||||||||||||||||
Peren 148 TAGCAGATCGGCCTGTAGCATCCTGCGATGCACCTAAGCATGATGCCGTACATTGCTCAG 207

Publi 280 CTATTTATTTTTGTCTTTGTCTTCAGCACCGTGATCGTCAGTTTACAGCAGAGGGTCGTA 339
          ||||||||||||||||||||||||||||||||||||||||||||||||||||||||||||
Peren 208 CTATTTATTTTTGTCTTTGTCTTCAGCACCGTGATCGTCAGTTTACAGCAGAGGGTCGTA 267

Publi 340 TTCACGGTGTTTTCTTGTAACAGATCTCCCTCTTTCTCTCTCAGAATTCAGAAATAGCC 399
          |||||||||||||||||||||||||||||||||||||||||||||||||||||||||||
Peren 268 TTCACGGTGTTTTCTTGTAACAGATCTCCCTCTTTCTCTCTCAGAATTCAGAAATAGCC 327

Publi 400 AACTTAATTGTACACTGATATGAGGTATTGAGGTGCATATGTGATATGTTTGT 452
          |||||||||||||||||||||||||||||||||||||||||||||||||||||
Peren 328 AACTTAATTGTACACTGATATGAGGTATTGAGGTGCATATGTGATATGTTTGT 380
```

Publi, sequence published in Andersen et al. (2006)
Peren, determined perennial ryegrass sequence A TaqMan®-based quantitative real-time PCR was designed to simultaneously amplify each of the annual and perennial ryegrass-specific LpVRN2_2 InDel (referred to as BDIRyeSNP3 (SEQ ID NO: 10 for annual and SEQ ID NO: 11 for perennial, respectively) and β-tubulin, a housekeeping gene common to both annual and perennial ryegrass, as an internal control (referred to as BDIRyeIC (SEQ ID NO: 12)), along with forward and reverse primers for the annual and perennial probes (SEQ ID NO: 13 and SEQ ID NO: 14, respectively) and the forward and reverse primers for the internal control probe BDIRyeIC (SEQ ID NO: 15 and SEQ ID NO: 16, respectively). Table 4 also shows the sequences of the probes, forward primers, and reverse primers.

TABLE 4

Primer and probe sequences used for the qPCR assay.

| Marker | Forward primer (5'-3') | Reverse primer (5'-3') | TaqMan (MGB) probe |
|---|---|---|---|
| BDIRyeSNP3 | GCTCAACGCCAT CAGTAATGG | CAGCTACATACA CCTGCCTTTCA | Annual specific probe: FAM-TGACCCTCCTTCC Perennial specific probe: VIC-TGACCCCCTCCTTC |
| BDIRyeIC | AAGCTCGCCCTCC TCCAGTTCTA | TCCTTCCTGAGCC TGGTGACCTT | NED-AAGGTCGACGACGGCACC |

The qPCR was conducted using an ABI 7500 Thermal Cycler (Applied Biosystems, Foster City, Calif.) under a "ddCt (Relative Quantitation) plate" mode. The ABI manual (part number 4347824, Revision C) contains detailed steps for conducting relative quantitation. Replicated PCR runs for each DNA sample were carried out to minimize errors during PCR set up. Each optimized PCR reaction (25 µl) contained 1×ABI gene expression master mix (catalog number 4369510), 600 nM BDIRyeSNP3 forward primer (SEQ ID NO: 13), 600 nM BDIRyeSNP3 reverse primer (SEQ ID NO: 14), 200 nM BDIRyeIC forward primer (SEQ ID NO: 15), 200 nM BDIRyeIC reverse primer (SEQ ID NO: 16), 200 nM BDIRyeSNP3 TaqMan® annual probe (SEQ ID NO: 10), 200 nM BDIRyeIC TaqMan® probe (SEQ ID NO: 12) and five microliters (25 ng/microliter) total genomic DNA. The thermal cycling parameters include two minutes at 50° C. for Amp-erase UNG activation, followed by initial denaturation at 95° C. for 10 minutes and 40 cycles of denaturation at 95° C. for 15 minutes, followed by annealing/extension at 60° C. for one minute. After PCR, RQ (relative quantitation) values for the test samples were obtained by running the ddCt (relative quantitation) study mode using averages of eight Ct values for a known control sample as calibrator. Finally, percent annual seed contamination for each sample was calculated using all eight RQ values (four DNA replications×two PCR replications) using the Seed Calc 7.1 statistical program. Complementary sites for the BDIRyeSNP3 forward primer (SEQ ID NO: 13) extend from base 46 to base 74, for the reverse primer (SEQ ID NO: 14) from base 99 to base 121, and for the BDIRyeSNP3 probe (SEQ ID NO: 10) extend from base 78 to base 90.

G. Example 7

Construction of Further Probes and Primers

Referring to Table 1, three InDels and 17 SNPs are present, each in bold font. Probes of at least 12 nucleotides are constructed so as to contain at least one InDel or SNP. For example, probes are constructed with each sequential permutation of the sequence of Table 1 for the annual and/or perennial ryegrass sequence. Thus probes are constructed to be specific for annual or for perennial ryegrass DNA. For each of these probes, forward and reverse primers are then constructed as known to the art so as to flank the probe.

H. Example 8

Construction of Other LPVRN2_2 Primers and Probes

A qPCR is conducted to determine the presence of a perennial seed contaminant in a seed lot of annual ryegrass and uses the same reagents and protocol as explained above for Example 6, except that the perennial probe (VIC-TGAC-CCCCTCCTTC) is used in place of the annual probe (FAM-TGACCCTCCTTCC) (See Table 4).

I. Example 9

Determination of Proportion of Contaminants in Ryegrass Samples

To determine whether the LpVRN2_2 marker with the annual ryegrass-specific TaqMan® probe (BDIRyeSNP3) could specifically detect annual and intermediate ryegrass varieties, 32 pure perennial, 26 annual, and two intermediate ryegrass varieties were tested on an individual plant basis using the real-time qualitative PCR assay. The study also included an additional nine intermediate plants found as a contaminant in a perennial ryegrass plot. As seen from FIG. 2, the marker effectively detected all annual and intermediate ryegrass varieties.

Additionally, the marker also consistently did not indicate a false positive for any perennial variety. The BDIRyeSNP3 perennial ryegrass-specific TaqMan® probe also detected all perennial varieties and a few intermediates, but did not result in a false positive for in any of the annual varieties tested (data not shown). While intermediate ryegrass plants can be distinguished from perennials by visual observation of plants due to growth habit, intermediate ryegrass plants can only be distinguished from annual plants visually in the F1 generation.

J. Example 10

Comparison of QPCR Assay Results to Known Samples

To determine the accuracy and expense of using the TaqMan® BDIRysSNP3 probe to determine annual and intermediate contamination in perennial ryegrass seed lots. DNA extracted from lots of 5000 seeds, as described above, was subjected to the TaqMan®-based quantitative real-time PCR method. Various proportions of annual ryegrass seeds (variety Gulf) were mixed into pure perennial seed lots at various levels, with a minimum of one annual seed per 5000 annual seeds. The accuracy of the real-time PCR assay was estimated using a range of 0.02%-50% level of contamination, using 21 perennial seed lots, which included validation samples from other seed companies as a part of the external validation (Table 5).

TABLE 5

Accuracy and sensitivity of new DNA test in estimating annual seed contamination in perennial seed lots.

| Validation Sample | Percent Estimation by PCR | SE± (%) | Validation key % (Equivalent No. of Annual Seeds/5000 Seeds) |
|---|---|---|---|
| A | 2.4242% | 0.00 | 2.50% (125/5000) |
| B | 0.0439% | 0.01 | 0.02% (1/5000) |
| C | 0.3665% | 0.00 | 0.50% (25/5000) |
| D | 1.2408% | 0.09 | 1.20% (60/5000) |
| E | 0.1717% | 0.01 | 0.10% (5/5000) |
| F | 2.1602% | 0.08 | 2.00% (100/5000) |
| G | 1.6679% | 0.09 | 1.60% (80/5000) |
| H | 2.9897% | 0.25 | 3.00% (150/5000) |
| I | 0.0000% | 0.00 | 0.00% (0/5000) |
| J | 0.0000% | 0.00 | 0.02% (1/5000) |
| K | 0.0768% | 0.01 | 0.10% (5/5000) |
| L | 0.3665% | 0.04 | 0.50% (25/5000) |
| M | 0.9330% | 0.11 | 1.00% (50/5000) |
| N | 2.1100% | 0.21 | 2.00% (100/5000) |
| O | 2.2128% | 0.23 | 2.50% (125/5000) |
| P | 0.0108% | 0.01 | 0% (0/5000) |
| Q | 39.0800% | 0.01 | 50.00% (2500/5000) |
| R | 24.1400% | 0.62 | 25.00% (1250/5000) |
| S | 14.4600% | 0.61 | 12.50% (625/5000) |
| T | 10.9900% | 0.15 | 6.25% (313/5000) |
| U | 71.1900% | 1.36 | 93.00% (4650/5000) |

The results shown in Table 5 indicated that estimations of annual ryegrass seed contamination were more accurate in the 0.04%-20% range, moderate between the 20%-50% range, and less accurate at above 50% contamination levels. Without being bound to any specific theory it is believed that the moderate to low accuracy at the higher percentage contamination levels could have been due to saturation of the fluorescence signal. However, high accuracy of estimation at low levels, such as those between 0%-20% of contamination, rather than high levels (above 20%), is critical for the seed industry and this test is designed mainly to address this problem.

K. Example 11

Comparison of QPCR with SRF

Table 6 shows the results of a comparison between the DNA test of this invention and results from the SRF test.

TABLE 6

Comparison of % estimation of annual ryegrass contamination in perennial ryegrass by DNA and SRF tests.

| Samples | Estimations based on DNA test | SE± (%) | Estimations based on SRF Test |
|---|---|---|---|
| BDI-1 | 2.2444% | 0.48% | 1.70% |
| BDI-2 | 1.2924% | 0.83% | 1.55% |
| BDI-3 | 0.1026% | 0.04% | 0.00% |
| BDI-4 | 4.4104% | 1.22% | 1.68% |
| BDI-5 | 0.0421% | 0.00% | 0.53% |
| BDI-6 | 0.0032% | 0.00% | 1.29% |
| BDI-7 | 0.4739% | 0.20% | 1.08% |
| BDI-8 | 1.7958% | 0.64% | 2.09% |
| BDI-9 | 1.2816% | 0.65% | 1.84% |
| BDI-10 | 1.5805% | 0.41% | 3.08% |
| BDI-11 | 4.0402% | 0.00% | 1.02% |
| BDI-12 | 1.6492% | 0.19% | 2.73% |
| BDI-13 | 0.1340% | 0.16% | 0.00% |
| BDI-14 | 1.3800% | 0.45% | 2.43% |
| BDI-15 | 65.8668% | 17.05% | 99.00% |
| BDI-16 | 2.1126% | 0.60% | 181/.94 |

TABLE 6-continued

Comparison of % estimation of annual ryegrass contamination in perennial ryegrass by DNA and SRF tests.

| Samples | Estimations based on DNA test | SE± (%) | Estimations based on SRF Test |
|---|---|---|---|
| BDI-17 | 50.0943% | 4.46% | 90%/labeled 10% perennial |
| BDI-18 | 0.4212% | 0.20% | 1.01% |
| BDI-19 | 0.0336% | 0.07% | 0.00 |
| BDI-20 | 36.1229% | 0.00% | Intermediate Forage 90% |
| BDI-21 | 0.0372% | 0.05% | 0.80 |
| BDI-22 | 0.0168% | 0.01% | 0.27% |
| BDI-23 | 1.2060% | 0.61% | 3.84 |
| BDI-24 | 63.9454% | 11.12% | 99.97 |
| BDI-25 | 0.9294% | 0.24% | 2.43 |
| BDI-26 | 5.7351% | 1.12% | 1.34 |
| BDI-27 | 2.3296% | 0.71% | 6.25 |
| BDI-28 | 2.7901% | 0.00% | 2.68 |
| BDI-29 | 7.5500% | 0.12% | 44.91 |

The difference in estimation of contamination levels between the DNA and SRF tests was expected, as the SRF test is inaccurate and typically does not provide accurate estimates due to the fact that the SRF trait is not specific to annual ryegrass. Accordingly, Table 6 shows the results of the comparison between the DNA-based test of this invention and the growout test for the perennial ryegrass seed lot BDI-29, which showed the greatest difference in estimation values between the DNA-based test (7.55%) and SRF (44.91%).

TABLE 7

Comparison between DNA and SRF tests

| Particulars | DNA Test | SRF Test |
|---|---|---|
| Accuracy | High | Low |
| Environmental Influence | No | Yes |
| Sample Size | 5000 seeds | 400 seedlings |
| Time Required for completion of test | 2 days | 14-21 days |
| Cost effective | Yes | Yes |
| Distinguish intermediates from annual ryegrass | Possible | No |
| Seed germination | Not required | Required |
| Seed grinding | Required | Not required |

K. Comparison to Growout Results

A growout test was conducted using 76 plants of the seed lot BDI-29 without pre-selection based on root fluorescence. Of these 76 plants, flowering was observed in four plants (5.3%). Hence, the growout test results indicated that the DNA test of this invention is more accurate in estimating annual ryegrass contamination. The relatively low level of contamination indicated by the growout test, as compared to the DNA test of this invention, could have been due to fewer number of plants (76) tested as against a 66-fold higher sample size (5000 seeds) used in DNA analysis.

6. Articles of Manufacture

The invention further provides for articles of manufacture to detect annual or intermediate ryegrass DNA. An article of manufacture according to the present invention can include primers and probes used to detect annual or intermediate ryegrass DNA, together with suitable packaging materials. Exemplary primers and probes for detection of annual and intermediate ryegrass DNA are capable of hybridizing to target nucleic acid molecules. Methods of designing primers and probes are disclosed herein and representative examples of primers and probes that amplify and hybridize to annual or perennial ryegrass nucleic acid molecules are provided. Articles of manufacture of the invention can also include one or more fluorescent moieties for labeling the probes or, alternatively, the probes supplied with a kit can be labeled. For example, an article of manufacture may include a donor fluorescent moiety for labeling one of the probes of this invention and an acceptor fluorescent moiety for labeling and other probe of this invention. As another example, a donor and acceptor fluorescent moiety may be present on a single probe. Examples of suitable FRET donor fluorescent moieties and corresponding acceptor fluorescent moieties are provided herein. Articles of manufacture of the invention may also contained a package insert and/or package label having instructions thereon for using the primers and probes of this invention to detect the presence of annual or intermediate ryegrass DNA in a sample. Articles of manufacture may additionally include reagents for carrying out the methods described herein, such as buffers, polymerase enzymes, cofactors, or agents to prevent contamination. Such reagents may be specific for one of the commercially available instruments in use and known to the art.

Because numerous modifications of this invention may be made without departing from the spirit thereof, the scope of the invention is not to be limited to the embodiments illustrated and described. Rather, the scope of the invention is to be determined by the appended claims and their equivalents.

REFERENCES

Andersen, J. R. and Lübberstedt, T. (2003). Functional markers in plants. *Trends Plant Sci.* 8: 554-560.

Andersen, J. R., Jensen, L. B., Asp, T. and Lübberstedt, T. (2006). Vernalization response in perennial ryegrass (*Lolium perenne* L.) involves orthologues of diploid wheat (*Triticum monococcum*) VRN1 and rice (*Oryza sativa*) Hd1. *Plant Mol. Biol.* 60: 481-494.

Armstead, I. P., Turner, L. B., Farell, M., Skøt, L., Gomez, P., Montoya, T., Donnison, I. S., King, I. P. and Humphreys, M. O. (2004). Synteny between a major heading-date QTL in perennial ryegrass (*Lolium perenne* L.) and the Hd3 heading-date locus in rice. *Theor Appl Genet.* 108: 822-828.

Charmet, G. and Balfourier, F. (1994). Isozyme variation and species relationships in the genus *Lolium* L. (ryegrasses, Graminaceae). *Theor Appl Genet.* 87: 641-649.

Floyd, D. J. and Barker, R. E. (2002). Change of ryegrass seedling root fluorescence expression during three generations o seed increase. *Crop Sci.* 42: 905-911.

Hall, M. H. (1992). Ryegrass. *Penn State Univ. Agron Facts*, 19: 1-4.

Heide, O. M. (1994). Control of flowering and reproduction in temperate grasses. *New Phytol.* 128: 347-362.

Jensen, L. B., Andersen, J. R., Frei, U., Xing, Y., Taylor, C., Holm, P. B and Lübberstedt, T. (2005). QTL mapping of vernalization response in perennial ryegrass (*Lolium perenne* L.) reveals co-location with an orthologue of wheat VRN1. *Theor Appl Genet.* 110: 527-536.

Jung, G. A., van Wijk, A. F. P., Hunt, W. F. and Watson, C. E. (1996). Ryegrasses. In: Moser, L. E., Buxton, D. R and Casler, M. D. (eds.) Cool-season forage grasses. *Agron Monogr.* 34. ASA, Madison, Wis., pp 605-641.

Karimoto, R. S., Axelrod, B., Wolinsky, J. and Schall, E. D. (1962). The structure of annuloline, a naturally occurring oxazole alkaloid. *Tetrahedron Lett.* 3: 83.

Martin, J., Storgaard, M., Andersen, C. H. and Nielsen, K.K. (2004). Photoperiodic regulation of flowering in perennial ryegrass involving a CONSTANCE-like homolog. *Plant Mol. Biol.* 56: 159-169.

Mummenhoff, K., et al. (2001). Chloroplast DNA phylogeny and biogeography of *Lepidium* (Brassicaceae). American Journal of Botany 88 (11):2051-2063.

Ng, C. T. et al. (2005). Multiplex Real-Time PCR Assay Using Scorpion Probes and DNA Capture for Genotype-Specific Detection of *Giardia lamblia* on Fecal Samples. *J. Clinical Microbiology*, March 2005, pp 1256-1260.

Nyquist, W. E. (1963). Fluorescent perennial ryegrass. *Crop Sci.* 3: 223-226.

Payne, R. C., Scott, J. A. and Koszykowski, T. J. (1980). An esterase isenzyme difference in seed extracts of annual and perennial ryegrass. *J Seed Tech.* 5: 15-22.

Studer, B. et al. (2006). Development of novel microsatellite marker for the grassland species *Lolium multiflorum, Lolium perenne* and *Festuca pratensis*. Molecular Ecology Notes 6:1108-1110.

Szuhai, K. et al. (2001). Simultaneous A8344G heteroplasmy and mitochondrial DNA copy number quantification in Myoclonus Epilepsy and Ragged-Red Fibers (MERRF) syndrome by a multiplex Molecular Beacon based real-time fluorescence PCR. *Nucleic Acids Research*, vol. 29, No. 3 e13.

Warnke, S. E., Barker, R. E., Brilman, L., Young, W. and Cook, R. (2002). Inheritance of supeoxide dismutase (Sod1) in a perennial×annual ryegrass cross and its allelic distribution among cultivars. *Theor Appl Genet.* 105: 1146-1150.

Warnke, S. E., Barker, R. E., Jung, G., Sim, S-C., Rouf Milan, M. A., Saha, M. C., Brilman, L. A., Dupal, M. P and Forster, J. W. (2004). Genetic linkage mapping of an annual×perennial ryegrass population. *Theor Appl Genet.* 109: 294-304.

Whitcombe, D., J. Theaker, S. P. Guy, T. Brown, and S. Little. 1999. Detection of PCR products using self-probing amplicons and fluorescence. Nat. Biotechnol. 17:804-807.

Yang, E. C. et al. (2004). Evidence for two independent lineages of *Griffithsia* (Ceraminaceae, Rhodophyta) based on plastic protein-coding psaA, psbA, and rbcL gene sequences. Molecular Phylogenetics and Evolution 31: 680-688.

What is claimed is:

1. A kit for identifying *Lolium multiflorum* or *L. hybridum* DNA, comprising:
    a probe comprising an isolated nucleic acid comprising the nucleotide sequence of SEQ ID NO: 10 and a reporter bound to said nucleic acid;
    a forward primer comprising an isolated nucleic acid comprising the nucleotide sequence of SEQ ID NO: 13; and
    a reverse primer comprising an isolated nucleic acid comprising the nucleotide sequence of SEQ ID NO: 14.

2. The kit of claim 1, wherein said reporter generates a fluorescent signal.

3. The kit of claim 1, further comprising Taq polymerase.

4. The kit of claim 3, further comprising an internal control probe and forward and reverse internal control primers.

5. A method of identifying *Lolium multiflorum* or *L. hybridum* DNA, comprising:
    amplifying DNA of a sample from a *L. perenne* seed lot;
    sensing a fluorescent signal generated during said amplification using a probe and forward and reverse primers, said probe comprising the nucleotide sequence of SEQ ID NO: 10 or SEQ ID NO: 11, said forward primer comprising nucleotide sequence of SEQ ID NO: 13, and said reverse primer comprising the nucleotide sequence of SEQ ID NO: 14; and
    using said fluorescent signal to estimate a proportion of *L. multiflorum* or *L. hybridum* seed in said seed lot.

6. A method of assessing contamination of a *Lolium perenne* seed lot, comprising:
    amplifying DNA of a sample from said *L. perenne* seed lot with a probe, a forward primer, and a reverse primer, said probe comprising the nucleotide sequence of SEQ ID NO: 10 or SEQ ID NO: 11, said forward primer comprising the nucleotide sequence of SEQ ID NO: 13, and said reverse primer comprising the nucleotide sequence of SEQ ID NO: 14; and
    estimating a proportion of *L. multiflorum* or *L. hybridum* seed in said sample by normalizing fluorescence energy emitted from said sample during amplification.

7. A kit for detecting the presence of *Lolium multiflorum* or *L. hybridum*, comprising:
    a probe annealing to *L. multiflorum* or *L. hybridum* DNA and comprising an isolated nucleic acid and a reporter, said nucleic acid comprising 12 sequential nucleotides from the nucleotide sequence of SEQ ID NO: 10 or SEQ ID NO: 11, said reporter bonded to said nucleic acid; and
    forward and reverse primers, said forward primer annealing to *L. multiflorum* or *L. hybridum* DNA upstream from said annealed probe and said reverse primer annealing to *L. multiflorum* or *L. hybridum* DNA at a complementary position downstream from said bound probe.

8. A method of detecting *Lolium multiflorum* or *L. hybridum*, comprising:

annealing a probe, a forward primer and a reverse primer to a DNA extraction obtained from a plant or seed of *L. multiflorum* or *L. hybridum*, wherein said probe comprises an isolated nucleic acid and a reporter bonded to said nucleic acid, said nucleic acid comprising 12 sequential nucleotides from the nucleotide sequence of SEQ ID NO: 10 or SEQ ID NO: 11, said reporter bonded to said nucleic acid; and detecting a presence or absence of a signal from said reporter during a polymerase chain reaction cycle.

9. A method of manufacturing a kit for detecting the presence of a *Lolium multiflorum* or *L. hybridum* seed or plant, comprising packaging a probe with a forward primer and a reverse primer, said probe comprising an isolated nucleic acid and a reporter bound to said nucleic acid, said nucleic acid comprising 12 sequential nucleotides from the nucleotide sequence of SEQ ID NO: 10 or SEQ ID NO: 11, said forward primer annealing to *L. multiflorum* or *L. hybridum* DNA upstream to a binding site of said probe, said reverse primer annealing to *L. multiflorum* or *L. hybridum* DNA at a complementary position downstream from said bound probe.

* * * * *

SEQUENCE LISTING

```
<160> NUMBER OF SEQ ID NOS: 33

<210> SEQ ID NO 1
<211> LENGTH: 389
<212> TYPE: DNA
<213> ORGANISM: Lolium multiflorum

<400> SEQUENCE: 1
tattagcttg aggggcaccc ctagaataaa gtaggtcggt cacttacgtg tggtcccatg      60
cgtgtaggtc ccacacatca gtgagcacaa gtcacgtgcg gtaggtaggc aaactcccag     120
caatcttctt tgtcaagtaa agactcgtcg tcaagactct ctctctctct ctctctctct     180
ctctctctct ctctctctct ctctctctct ctctcccttg tgtcgctgaa aaaaaatgaa     240
tattagacgg gcgcgtagcc cgctctgcgg gtatacataa ctgaaaccct gtgtgccagt     300
caacatcact caccgaaaaa agtgaagcgt ttcttttcac cataaataac agcgccccg      360 tgaggcactg ctctcccttt ctcttaatt                                        389

<210> SEQ ID NO 2
<211> LENGTH: 20
<212> TYPE: DNA
<213> ORGANISM: Lolium multiflorum

<400> SEQUENCE: 2
tgcgtgtagg tcccacacat                                                   20

<210> SEQ ID NO 3
<211> LENGTH: 21
<212> TYPE: DNA
<213> ORGANISM: Lolium multiflorum

<400> SEQUENCE: 3
gctacgcgcc cgtctaatat t                                                 21

<210> SEQ ID NO 4
<211> LENGTH: 1284
<212> TYPE: DNA
<213> ORGANISM: Lolium perenne
```

```
<400> SEQUENCE: 4
gttgttgttc gcccctcctc tcctcttctt ccccactgga cgaacgccat gacaccggcc      60
ccacggctcc acctgcaccc tcgggactag ccgtcgccgt cgccgtccgg gcgggttgtg     120
gattagggtt tggtctgctc ttcgttcgag ggagggaggc gagatggggc gcggcaaggt     180
gcagctcaag cggatcgaga acaagatcaa ccgccaggtc accttctcca agcgccgctc     240
ggggctgctc aagaaggcgc acgagatctc cgtgctctgc gacgccgagg tcgggctcat     300
catcttctcc accaagggaa agctctacga gttcgcaacc gactcatgta tggacaaaat     360
tcttgagcgg tatgagcgct actcctatgc agagaaagtg ctcatttcaa ccgaatctga     420
aattcaggga aactggtgtc atgaatatag gaaactgaag gcgaaggttg agacaataca     480
gagatgtcaa aagcatctaa tgggagagga tcttgaatca ttgaatctca aggagttgca     540
gcaactagag cagcagctgg aaagttcact gaaacatatt agagccagaa agaaccagct     600
tatgcacgaa tccatatctg agcttcaaaa gaaggagagg tcactgcagg aggagaataa     660
aattctccag aaggaactca tagagaagca gaaggcccac acgcagcaag cgcagtggga     720
gcaaactcag ccccaaacca gctcttcctc ctcctccttt atgatggggg aagctacccc     780
agcaacaaat tgcagtaatc ccccagcagc ggccagcgac agagcagagg atgcgacggg     840
gcagccttca gctcgcacgg tgcttccacc atggatggtg agtcacatca acaatggctg     900
aaggggcctt ccactccatc taaacgtatt attcagtacg tgtagcgagc tgcaccggcc     960
tgtcttcttg tggttgctag caagctgacc cctagaggaa agcagaaagg gaaaattcgg    1020
agaaaggtag caggttgcaa tgtgtatatt tcactctgtt ctgctcagtt tccctcctgc    1080
gtgagctgac ttcacgtaag agttatttaa cttgtaatac atgtgtagcg tgagtgacaa    1140
attttccact ttctacgacc ctcttgggta ccgtctgttt ctgtgaatta aactatccaa    1200
tatgagtatt atgtatattg tgattgttga aaataaatta atctggacct ttgtctccgt    1260
gatcttaaaa aaaaaaaaaa aaaa                                          1284

<210> SEQ ID NO 5
<211> LENGTH: 19
<212> TYPE: DNA
<213> ORGANISM: Lolium perenne

<400> SEQUENCE: 5
gtcagcagta gcagagcaa                                                  19

<210> SEQ ID NO 6
<211> LENGTH: 23
<212> TYPE: DNA
<213> ORGANISM: Lolium perenne

<400> SEQUENCE: 6
tgggactccc gcctgtcctc cca                                             23

<210> SEQ ID NO 7
<211> LENGTH: 375
<212> TYPE: DNA
<213> ORGANISM: Lolium multiflorum

<400> SEQUENCE: 7
agtccggtat ttatagcgga acacggagcg ggtgaaagga cgttttgtca gtcgaatgaa      60
gctctcaacg ccatcagtaa tgggggatga ccctccttcc tcgccctctg aaaggcaggt     120
gtatgtagct gggttttttcc atgtagcaga ttggcctgta gcatcctacg atgcacctaa     180
```

```
gcatgatgcc gtacattgct cagctattta ttttagtctt tcttcagcac cgtgatcgtc    240
agtttacagc agaggtttgt attcacggtg cttttcttgt aacaaatctc cctttttctc    300
tctcagaact cggaaatagc caacttaatt gtacactgat atgaggtatt gaggtgcata    360
tgtgatatgt ttgta                                                     375

<210> SEQ ID NO 8
<211> LENGTH: 375
<212> TYPE: DNA
<213> ORGANISM: Lolium multiflorum

<400> SEQUENCE: 8
agtccggtat ttatagcgga acacggagcg ggtgaaagga cgttttgtca gtcgaatgaa    60
gctctcaacg ccatcagtaa tgggggatga ccctccttcc tcgccctctg aaaggcaggt    120
gtatgtagct gggttttttcc atgtagcaga ttggcctgta gcatcctacg atgcacctaa    180
gcatgatgcc gtacattgct cagctattta ttttagtctt tcttcagcac cgtgatcgtc    240
agtttacagc agaggtttgt attcacggtg cttttcttgt aacaaatctc cctttttctc    300
tctcagaact cggaaatagc caacttaatt gtacactgat atgaggtatt gaggtgcata    360
tgtgatatgt ttgta                                                     375

<210> SEQ ID NO 9
<211> LENGTH: 383
<212> TYPE: DNA
<213> ORGANISM: Lolium perenne

<400> SEQUENCE: 9
ctgatgtgtt atttgtagcg gaacacggag cgggtgaaag gtcgttttgt cagtcgaatg    60
aagcgctcaa tgccagcagt aatggtggat gacccctcc ttcctcgccc tctgagaggc    120
agctgtatgt agctgggtt ttccatgtag cagatcggcc tgtagcatcc tgcgatgcac    180
ctaagcatga tgccgtacat tgctcagcta tttattttg tctttgtctt cagcaccgtg    240
atcgtcagtt tacagcagag gtcgtattc acggtgtttt tcttgtaaca gatctccctc    300
tttctctctc agaattcaga aatagccaac ttaattgtac actgatatga ggtattgagg    360
tgcaatatgt gatatgtttg tac                                            383

<210> SEQ ID NO 10
<211> LENGTH: 13
<212> TYPE: DNA
<213> ORGANISM: Lolium multiflorum

<400> SEQUENCE: 10
tgaccctcct tcc                                                       13

<210> SEQ ID NO 11
<211> LENGTH: 14
<212> TYPE: DNA
<213> ORGANISM: Lolium perenne

<400> SEQUENCE: 11 tgacccccte ctte                                                      14

<210> SEQ ID NO 12
<211> LENGTH: 18
<212> TYPE: DNA
<213> ORGANISM: Lolium spp.

<400> SEQUENCE: 12
```

-continued

```
aaggtcgacg acggcacc                                                   18

<210> SEQ ID NO 13
<211> LENGTH: 21
<212> TYPE: DNA
<213> ORGANISM: Lolium multiflorum

<400> SEQUENCE: 13
gctcaacgcc atcagtaatg g                                               21

<210> SEQ ID NO 14
<211> LENGTH: 23
<212> TYPE: DNA
<213> ORGANISM: Lolium perenne

<400> SEQUENCE: 14
cagctacata cacctgcctt tca                                             23

<210> SEQ ID NO 15
<211> LENGTH: 23
<212> TYPE: DNA
<213> ORGANISM: Lolium spp.

<400> SEQUENCE: 15
aagctcgccc tcctccagtt cta                                             23

<210> SEQ ID NO 16
<211> LENGTH: 23
<212> TYPE: DNA
<213> ORGANISM: Lolium spp.

<400> SEQUENCE: 16
tccttcctga gcctggtgac ctt                                             23

<210> SEQ ID NO 17
<211> LENGTH: 47
<212> TYPE: DNA
<213> ORGANISM: Lolium multiflorum

<400> SEQUENCE: 17
cgattaatct tccaatatgc taggttcaac aactctcgtt ctttaca                   47

<210> SEQ ID NO 18
<211> LENGTH: 47
<212> TYPE: DNA
<213> ORGANISM: Lolium perenne

<400> SEQUENCE: 18
cgattaatct tccaatatgc taggttcaac aactctcgtt ctttaca                   47

<210> SEQ ID NO 19
<211> LENGTH: 47
<212> TYPE: DNA
<213> ORGANISM: Lolium multiflorum

<400> SEQUENCE: 19
tgtaaagaac gagagttgtt gaacctagca tattggaaga ttaatcg                   47

<210> SEQ ID NO 20
<211> LENGTH: 47
<212> TYPE: DNA
<213> ORGANISM: Lolium perenne

<400> SEQUENCE: 20
```

```
tgtaaagaac gagagttgtt gaaactagca tattggaaga ttaatcg         47
```

<210> SEQ ID NO 21
<211> LENGTH: 945
<212> TYPE: DNA
<213> ORGANISM: Lolium perenne

<400> SEQUENCE: 21

```
cctccagtag atattgatgg tattcgtgag cctgtttctg gttctttact ttatggaaac    60
aatattatct ctggtgctat tattcctact tcggcggcga tcggattgca cttttaccca   120
atttgggaag ctgcatctgt tgatgagtgg ttatacaatg gtggtcctta tgagctaatt   180
gttctacact tcttacttgg tgtagcttgt tatatgggtc gtgagtggga acttagtttc   240
cgtttgggta tgcgtccttg gattgctgtt gcatactcag ctcctgttgc ggctgctact   300
gctgttttct tgatttaccc tattggtcaa ggaagcttct ctgatggtat gcctttagga   360
atatctggta ctttcaactt tatgattgta ttccaggcag agcacaacat ccttatgcat   420
ccattccaca tgttaggtgt agctggtgta ttcggcggct ccctatttag tgctatgcat   480
ggttccttgg taacctctag tttgatcagg gaaactactg aaaatgaatc tgctaatgag   540
ggttacaaat ttggtcaaga ggaagagact tataatattg tggctgctca tggttatttt   600
ggccgattaa tcttccaata tgctagtttc aacaactctc gttctttaca cttcttcttg   660
gctgcttggc ctgtagtagg aatctggttc actgctttag gtattagtac tatggctttc   720
aacctaaatg gtttcaattt caaccaatct gtagttgata gtcaaggtcg cgttattaat   780
acttgggctg atatcatcaa ccgagctaat cttggtatgg aagtaatgca cgaacgtaat   840
gctcacaact ccctctaga cctagctgct cttgaagttc catctcttaa tggataaggt   900
ttttctgcta acatatagga attttgaag aaaaaaaaaa aaaaa                    945
```

<210> SEQ ID NO 22
<211> LENGTH: 60
<212> TYPE: DNA
<213> ORGANISM: Lolium multiflorum

<400> SEQUENCE: 22

```
ggtatagtat aggaaatccg taaaatatca gatcttattt attaatctta gctattaact    60
```

<210> SEQ ID NO 23
<211> LENGTH: 60
<212> TYPE: DNA
<213> ORGANISM: Lolium perenne

<400> SEQUENCE: 23

```
ggtatagtat aggaaatccg taaaatctca gatcttattt attaatctta gctattaact    60
```

<210> SEQ ID NO 24
<211> LENGTH: 60
<212> TYPE: DNA
<213> ORGANISM: Lolium multiflorum

<400> SEQUENCE: 24

```
agttaatagc taagattaat aaataagatc tgatatttta cggatttcct atactatacc    60
```

<210> SEQ ID NO 25
<211> LENGTH: 60
<212> TYPE: DNA
<213> ORGANISM: Lolium perenne

<400> SEQUENCE: 25

```
agttaatagc taagattaat aaataagatc tgagatttta cggatttcct atactatacc    60
```

<210> SEQ ID NO 26
<211> LENGTH: 60
<212> TYPE: DNA
<213> ORGANISM: Lolium multiflorum

<400> SEQUENCE: 26

```
gaacttttt ttatttctct aattagcaaa tacattttc tatatagaat ggatttgatt    60
```

<210> SEQ ID NO 27
<211> LENGTH: 60
<212> TYPE: DNA
<213> ORGANISM: Lolium perenne

<400> SEQUENCE: 27

```
gaactttttt ttatttctct aattagcaaa tgcattttc tatatagaat ggatttgatt    60
```

<210> SEQ ID NO 28
<211> LENGTH: 60
<212> TYPE: DNA
<213> ORGANISM: Lolium multiflorum

<400> SEQUENCE: 28

```
aatcaaatcc attctatata gaaaatgta tttgctaatt agagaaataa aaaaaagttc    60
```

<210> SEQ ID NO 29
<211> LENGTH: 60
<212> TYPE: DNA
<213> ORGANISM: Lolium perenne

<400> SEQUENCE: 29

```
aatcaaatcc attctatata gaaaatgca tttgctaatt agagaaataa aaaaaagttc    60
```

<210> SEQ ID NO 30
<211> LENGTH: 713
<212> TYPE: DNA
<213> ORGANISM: Lolium multiflorum

<400> SEQUENCE: 30

```
gtgggcttac atagcagaaa tagtgtaaca aatagaaata ggtatagtat aggaaatccg    60
taaaatatca gatcttattt attaatctta gctattaact agttcgaaat ttaaagttcg   120
acttatactt aataatactt ataaaaaaaa atactaaaac ttcttacaga taaagttagc   180
ttgatatgct taagtagaag atatctttaa ataaaattat agaatttatt gaactttttt   240
ttatttctct aattagcaaa tacattttc tatatagaat ggatttgatt ccaatttcta   300
taatggaatt ggatttcaga tattttcaat ttgatatggc tcggacgaat aatctaatac   360
atagaaaaga ataatatata tatgaaagat ataataaaga gaaaatacaa atttattggc   420
attttcattc gatcattatc gactttattt tgagatattt ttttattttgt aaataatttg   480
agaattccta tttaactaag gagaacatag agtcatagca ataaaattg ctaattctga   540
ttagaaaaaa aaaattaata tcaagcgtta gtatatgatt ttaaatactc taaaaaagtc   600
ataaagggg tcggggagag aaaaactttt ggatatattg attcggattg aattgcaaat   660
acatcaacga tacaatcaat tcaattctga attgcaataa gcaagcggtg tct        713
```

<210> SEQ ID NO 31
<211> LENGTH: 420
<212> TYPE: DNA
<213> ORGANISM: Lolium multiflorum

```
<400> SEQUENCE: 31
gtcagcagta gcagagcaac actttttttt tttttgaggg taaaacacaa tatattaagc    60
tagcaagccg cctcattaaa aaccttccag tccccttcgg taccctggta aggaaaagag   120
tgcgtctgaa acttgctgcc cgagttcaaa acagagttac atcagcaatt acatctgaaa   180
gcacatgatc aggaggatca tcatcccaaa ctataactcg tgcagcctca aaactaaacc   240
tagctaaatt gtgagctacc ctattagact ccctaggaca gtaagcaaaa gaaacagctc   300
ctaatctttg tatgacccca ctactgtcag cagtagcaga gcaacacttg aaagtccaca   360
aatcaatcat gaatcatgcg cacgagacga cgcaggcagg gaggacaggc gggagtccca   420

<210> SEQ ID NO 32
<211> LENGTH: 95
<212> TYPE: DNA
<213> ORGANISM: Lolium perenne

<400> SEQUENCE: 32
gtcagcagta gcagagcaac acttgaaagt ccacaaatca atcatgaatc atgcgcacga    60
gacgacgcag gcagggagga caggcgggag tccca                               95

<210> SEQ ID NO 33
<211> LENGTH: 278
<212> TYPE: DNA
<213> ORGANISM: Lolium perenne

<400> SEQUENCE: 33
gatcaagggc cgcttcgcga aaatatcaga agcggaaatg gaagtggacc agatgttctc    60
ggctgcagct ctttctgaca gtagctacag tactgttccc tggtttcaat gagactctat   120
tagacattac attagcatat atatgtactt accagaacaa taaggaccag tgcaagcagt   180
tcaggtagat cggtgctctg aataattgtg tggtatgcga accttaattg ataaggtatc   240
ttagtatcaa aaaaaaaaa aaaaaaaaaa aaaaaaaa                             278
```